US012565539B2

(12) United States Patent
Saito et al.

(10) Patent No.: US 12,565,539 B2
(45) Date of Patent: *Mar. 3, 2026

(54) METHOD FOR PRIMARY PREVENTION OF ALLERGIC DISORDERS DURING INFANCY THROUGH IgE-CLASS-SPECIFIC IMMUNOSUPPRESSION

(71) Applicants: HUBIT GENOMIX, INC., Tokyo (JP); NATIONAL CENTER FOR CHILD HEALTH AND DEVELOPMENT, Tokyo (JP); Yutaka Ishizaka, Carlisle, MA (US)

(72) Inventors: Hirohisa Saito, Saitama (JP); Kenji Matsumoto, Tokyo (JP); Hideaki Morita, Tokyo (JP); Go Ichien, Tokyo (JP); Yasuhiko Koezuka, Tokyo (JP); Kimishige Ishizaka, Carlisle, MA (US)

(73) Assignees: HUBIT GENOMIX, INC., Tokyo (JP); NATIONAL CENTER FOR CHILD HEALTH AND DEVELOPMENT, Tokyo (JP); Yutaka Ishizaka, Carlisle, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/516,127

(22) Filed: Nov. 21, 2023

(65) Prior Publication Data

US 2025/0163185 A1     May 22, 2025

Related U.S. Application Data

(63) Continuation of application No. 16/841,527, filed on Apr. 6, 2020, now Pat. No. 11,827,719, which is a continuation of application No. PCT/JP2018/039614, filed on Oct. 25, 2018.

(30) Foreign Application Priority Data

Nov. 7, 2017    (JP) ................................. 2017-214455

(51) Int. Cl.
    *C07K 16/42*      (2006.01)
    *A61P 37/08*      (2006.01)

(52) U.S. Cl.
    CPC .......... *C07K 16/4291* (2013.01); *A61P 37/08* (2018.01)

(58) Field of Classification Search
    None
    See application file for complete search history.

(56) References Cited

U.S. PATENT DOCUMENTS

| | | | | |
|---|---|---|---|---|
| 7,871,624 B2 * | 1/2011 | Grubb | ..................... | A61P 43/00 |
| | | | | 424/134.1 |
| 8,071,097 B2 * | 12/2011 | Wu | ......................... | A61P 33/00 |
| | | | | 424/139.1 |
| 8,137,670 B2 * | 3/2012 | Wu | ......................... | A61P 11/06 |
| | | | | 424/139.1 |
| 10,047,166 B2 * | 8/2018 | Chen | .................. | C07K 16/2851 |
| 11,827,719 B2 * | 11/2023 | Saito | ....................... | A61P 37/08 |
| 2002/0006402 A1 * | 1/2002 | Anderson | .......... | C07K 16/4291 |
| | | | | 424/131.1 |

FOREIGN PATENT DOCUMENTS

| | | | | |
|---|---|---|---|---|
| EA | 011302 B1 | 2/2009 | | |
| EA | 018068 B1 | 5/2013 | | |
| JP | H06-500780 A | 1/1994 | | |
| WO | 02/04053 A1 | 3/1992 | | |
| WO | 01/51076 A1 | 7/2001 | | |
| WO | WO-03057249 A1 * | 7/2003 | .......... | A61K 31/436 |
| WO | WO-2005078442 A1 * | 8/2005 | .......... | G01N 33/537 |
| WO | WO-2019093137 A1 * | 5/2019 | .......... | A61K 39/395 |

OTHER PUBLICATIONS

Janeway et al., Immunobiology, 3rd edition, Garland Publishing Inc., 1997, pp. 8:18-8:19.*

Vaughn et al., Structure. Jan. 15, 1998;6(1):63-73. doi: 10.1016/s0969-2126(98)00008-2. PMID: 9493268.*

Pyzik et al., J Immunol. May 15, 2015;194(10):4595-603. doi: 10.4049/jimmunol.1403014. PMID: 25934922 PMCID: PMC4451002.*

International Search Report issued in related International Patent Application No. PCT/JP2018/039614 dated Dec. 18, 2018.

Dufour et al., "Successful management of severe infant bullous pemphigoid with malizumab," British Journal of Dermatology, 166 (5): 1140-1142 (2012).

Nigro et al., "Passive Immunization during Pregnancy for Congenital Cytomegalovirus Infection," The New England Journal of Medicine, 353 (13): 1350-1362 (2005).

Kuehr et al., "Efficacy of combination treatment with anti-IgE plus specific immunotherapy in polysensitized children and adolescents with seasonal allergic rhinitis," Journal of Allergy Clinical Immunology, 109 (2): 274-280 (2002).

Partial Supplementary European Search Report issued in corresponding European Patent Application No. 18875171.3 dated Jul. 30, 2021.

Pawankar et al., "Overview on the pathomechanisms of allergic rhinitis," Asia Pacific Allergy, 157-167 (2011).

Haba et al., "Inhibition of IgE synthesis by anti-IgE: Role in long-term inhibition of IgE synthesis by neonatally administered soluble IgE," PNAS, 87: 3363-3367 (1990).

Vassella et al., "High anti-IgE levels at birth are associated with a reduced allergy prevalence in infants at risk: a prospective study," Clinical and Experimental Allergy, 24: 771-777 (1994).

Glovsky et al., "Effect of maternal immunotherapy on immediate skin test reactivity, specific rye I IgGE and IgE antibody, and total IgE of the children," Annals of Allergy, 67: 21-24 (1991).

McBain et al., "Anti-D administration in pregnancy for preventing Rhesus alloimmunisation," The Cochrane Database of Systematic Reviews, 9: CD000020 (2015).

Morita et al., "IgE-class-specific immunosuppression in offspring by administration of anti-IgE to pregnant mice," Journal of Allergy and Clinical Immunology, 143 (3): 1261-1264 (2019).

(Continued)

*Primary Examiner* — Michael Szperka

(74) *Attorney, Agent, or Firm* — Morgan, Lewis & Bockius LLP

(57) ABSTRACT

The disclosure provides a pharmaceutical composition containing an anti-IgE antibody that suppresses the production of allergen-specific IgE antibodies and methods of use thereof.

17 Claims, 10 Drawing Sheets

(56) References Cited

OTHER PUBLICATIONS

English translation of Office Action issued in corresponding Russian Patent Application No. 2020113059 dated Jun. 15, 2022.
English translation of Search Report issued in corresponding Russian Patent Application No. 2020113059 dated Jun. 15, 2022.
Janeway CA Jr, Travers P, Walport M. et al. Immunobiology: The Immune System in Health andDisease. 5th edition, New York: Garland Science; 2001 (Year: 2001).
Bosquet, J., et al. European Respiratory Review 17,107 (2008): 109 (Year: 2008).
Palmeira, Patricia et al. Clinical & developmental immunology vol. 2012 (2012): 985646 (Year: 2012).
Normansell, Rebecca, et al., Cochrane database of systematic reviews 1 (2014) (Year: 2014).

* cited by examiner

[Figure 1]
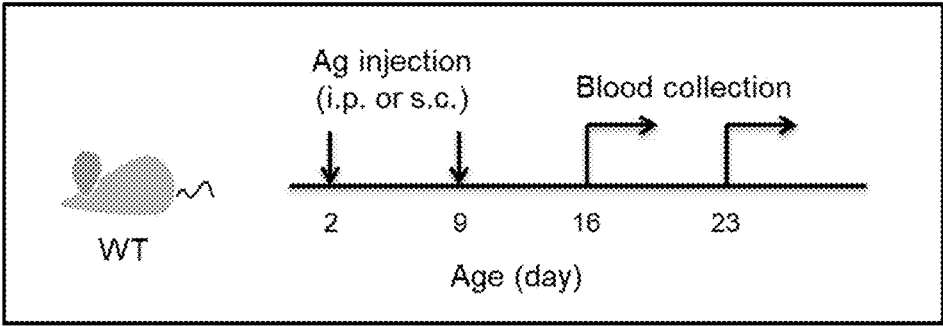
[Figure 2]
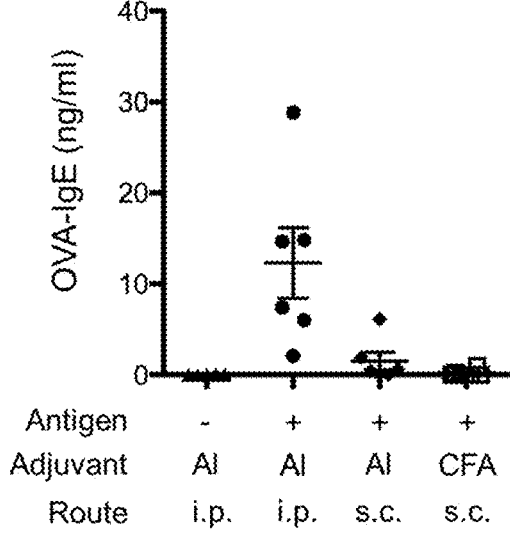
[Figure 3]
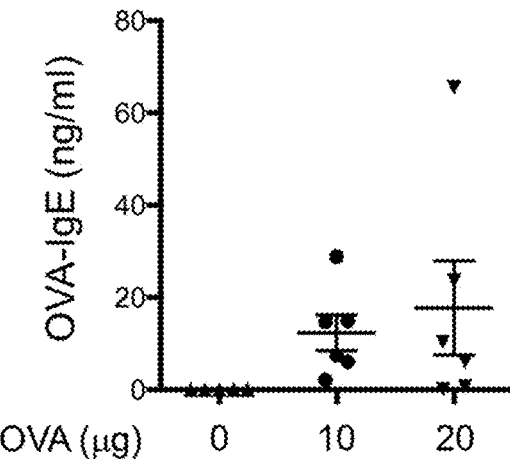

[Figure 4]
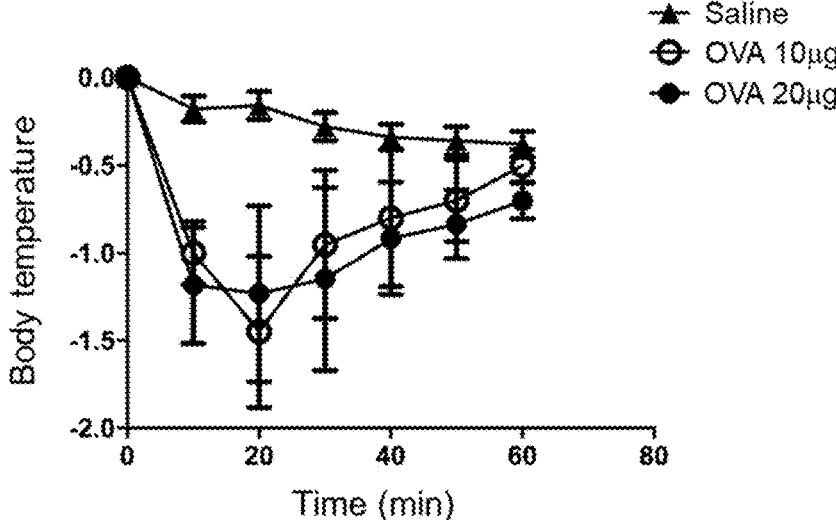
[Figure 5]
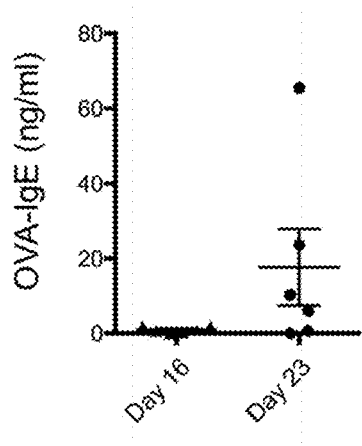
[Figure 6]
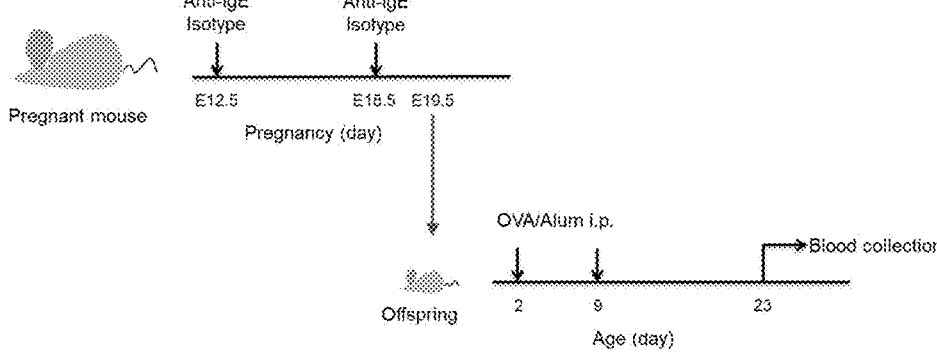

[Figure 7]
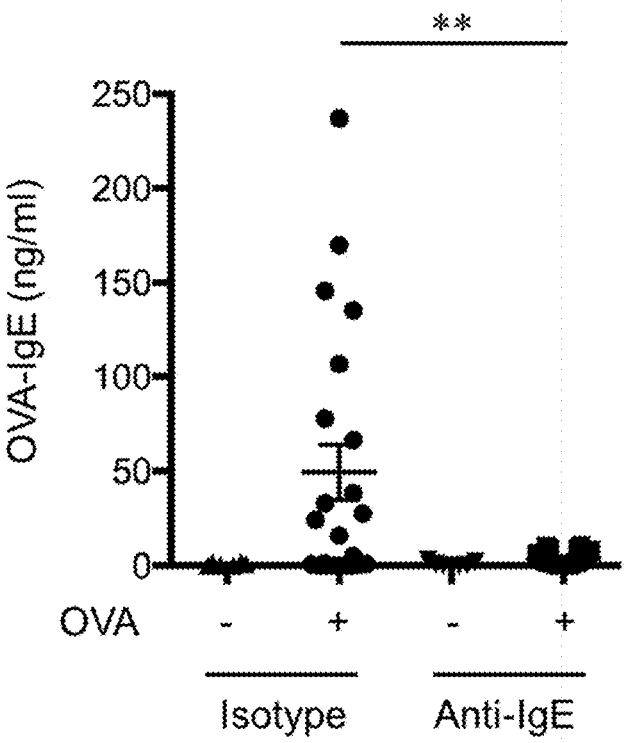
[Figure 8]
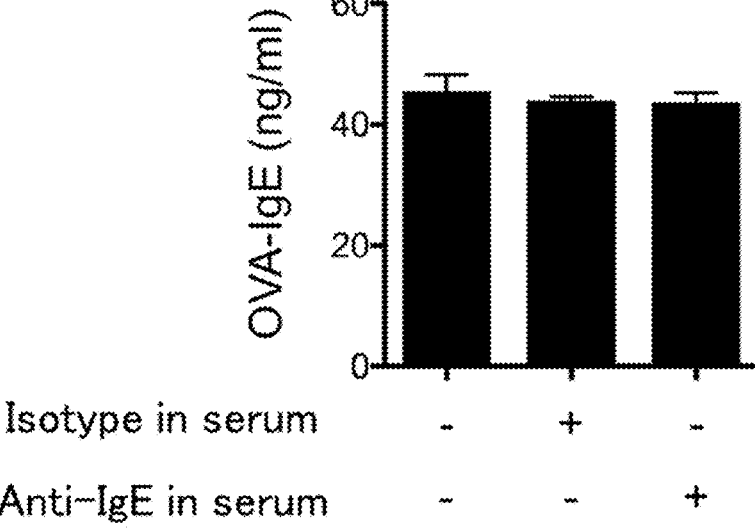

[Figure 9]
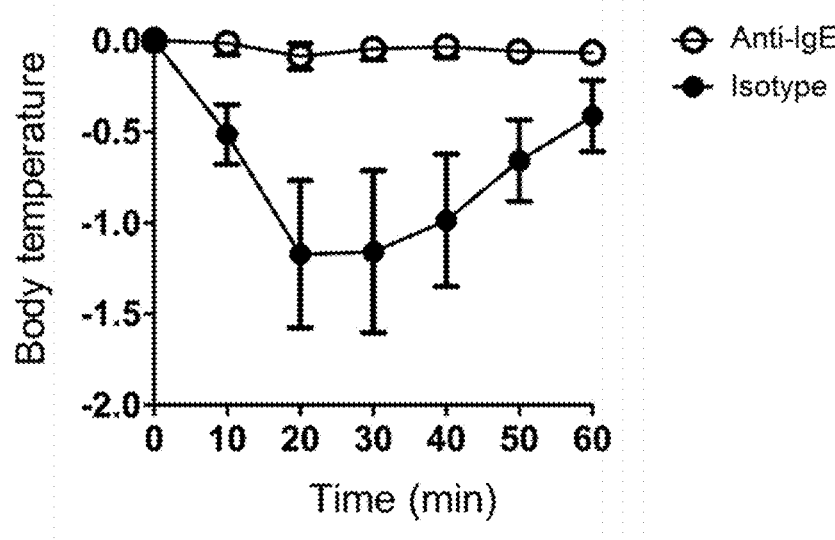
[Figure 10]
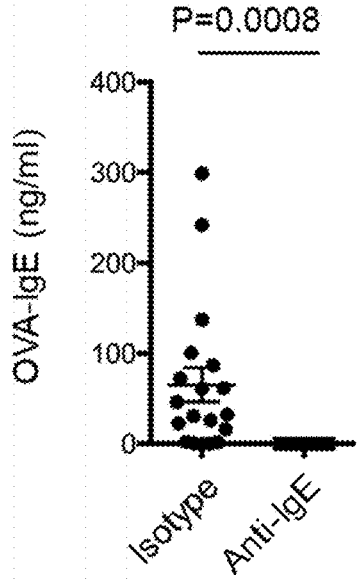

[Figure 11]
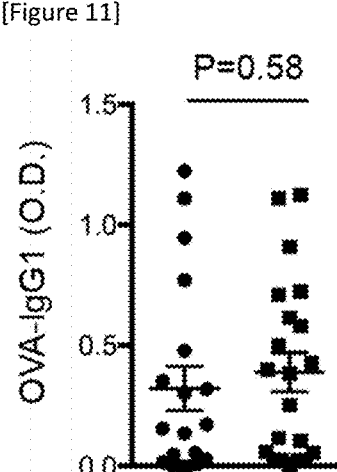
[Figure 12]
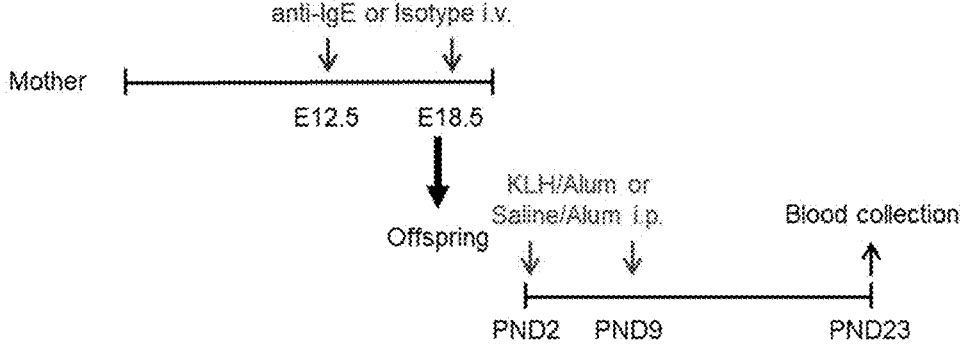
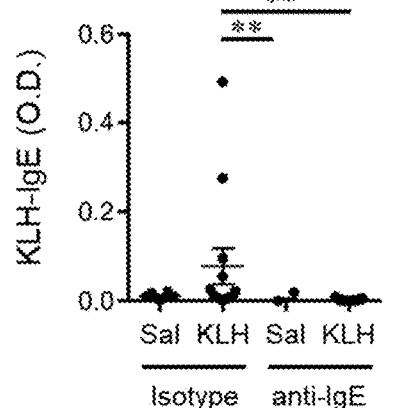
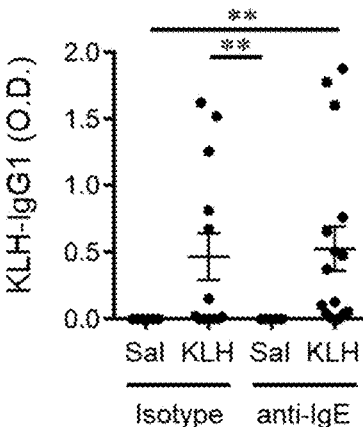

[Figure 13]
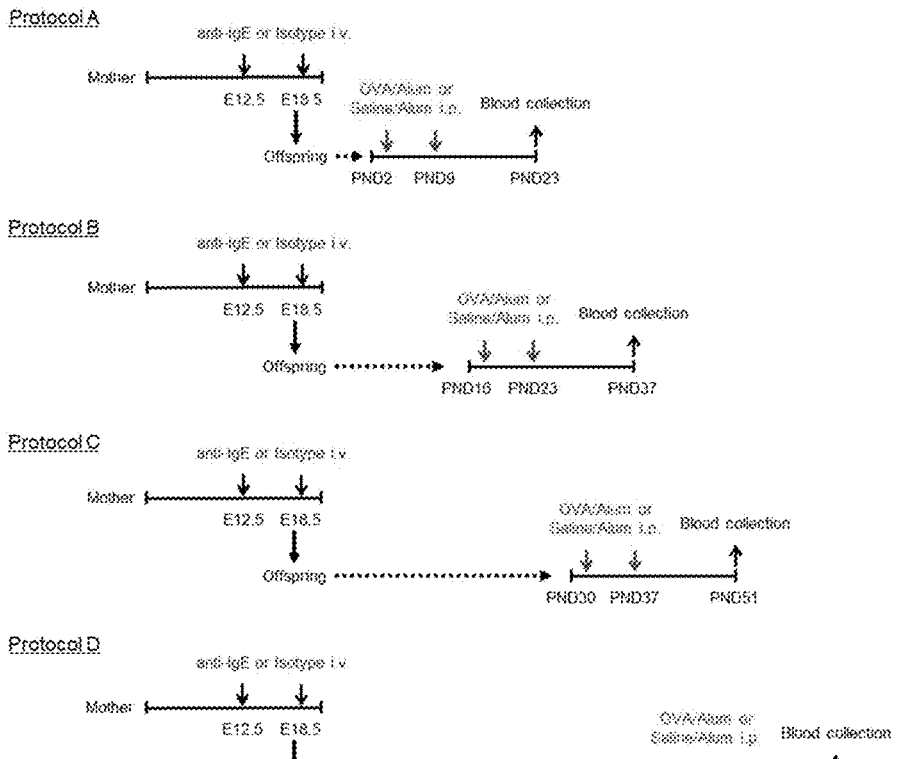
[Figure 14]
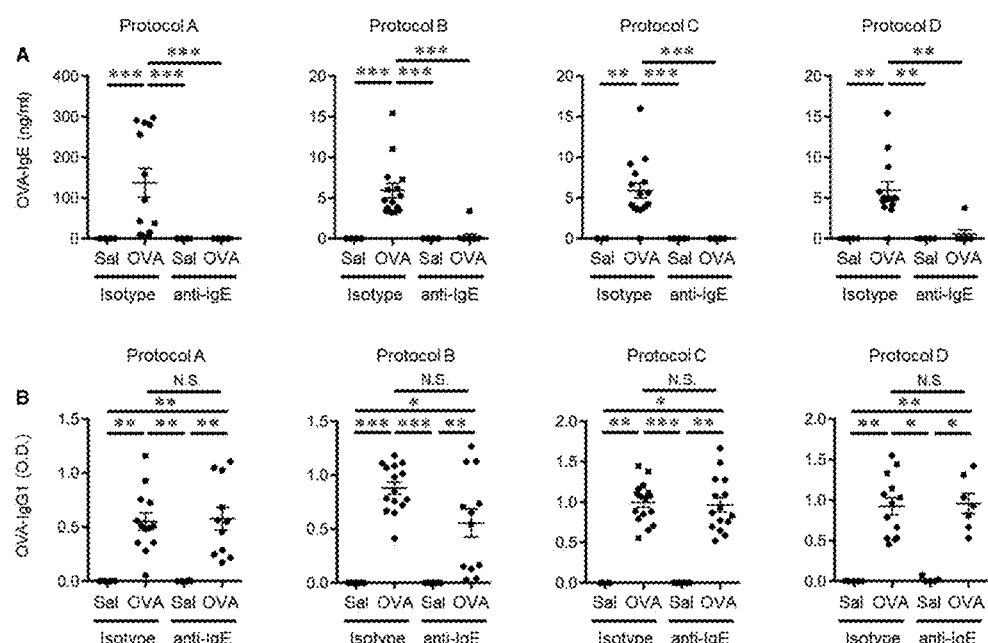

[Figure15]
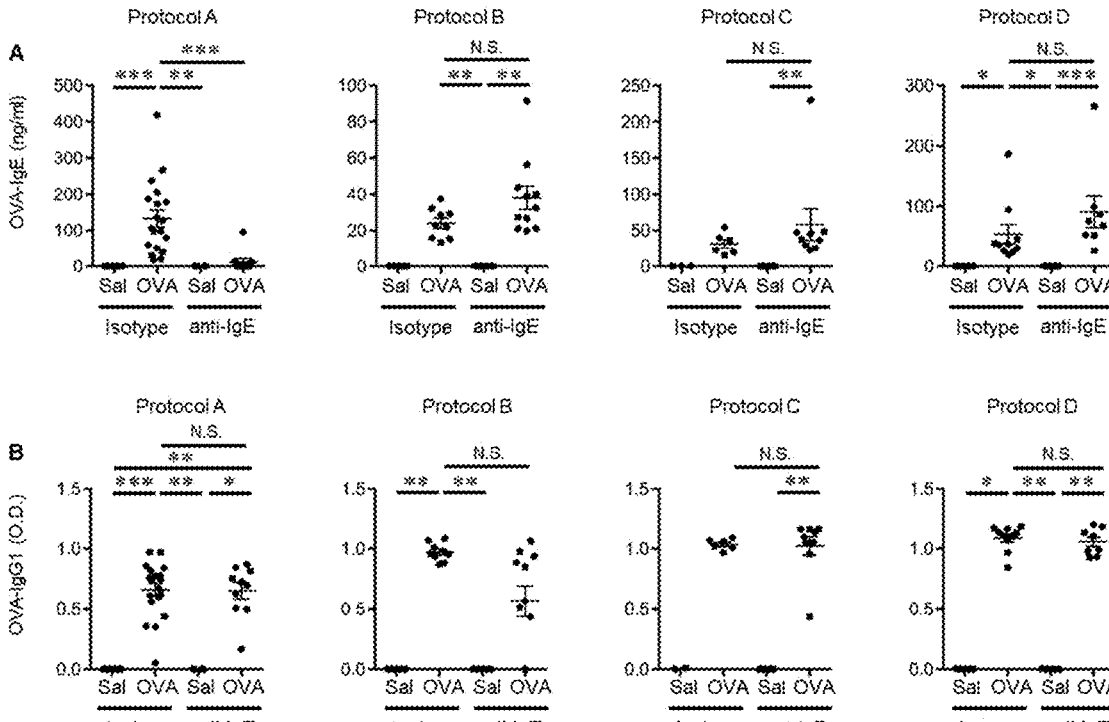
[Figure 16]
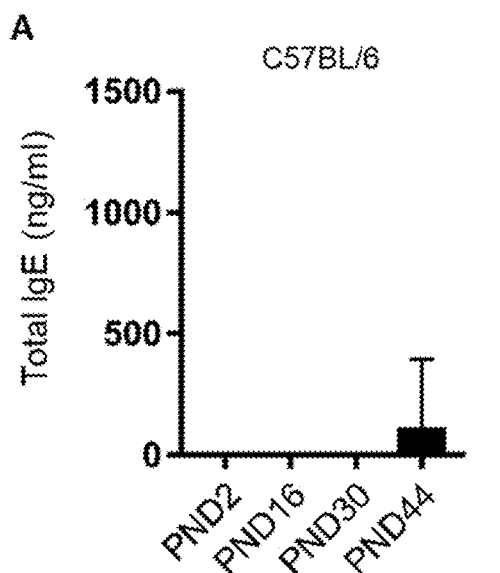
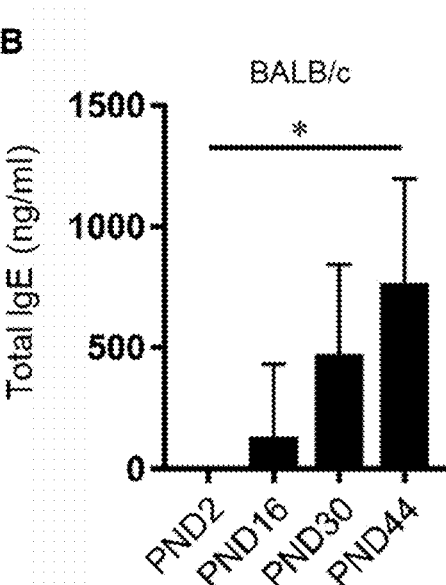

[Figure 17]
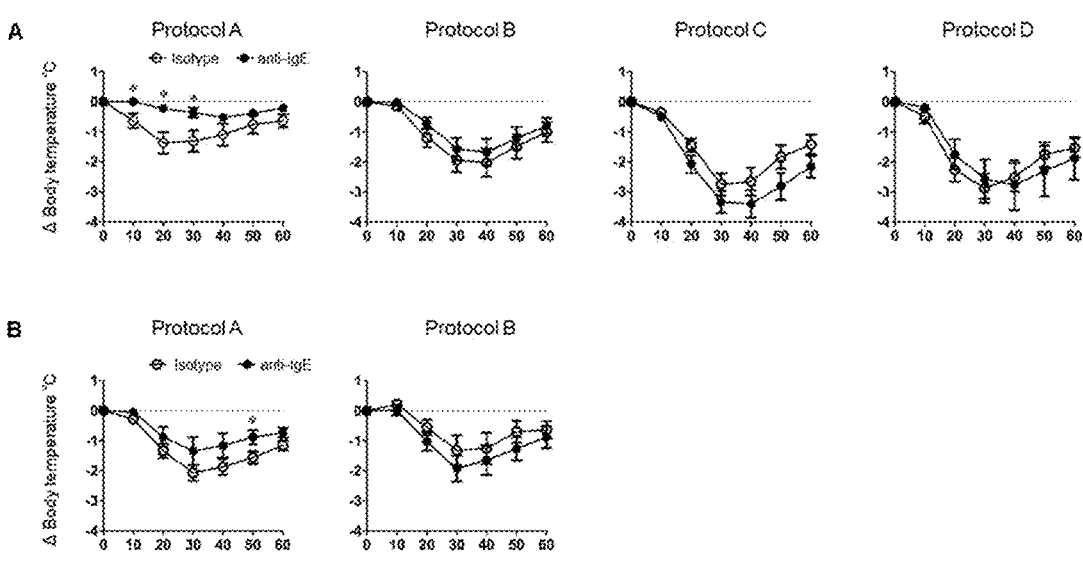
[Figure 18]
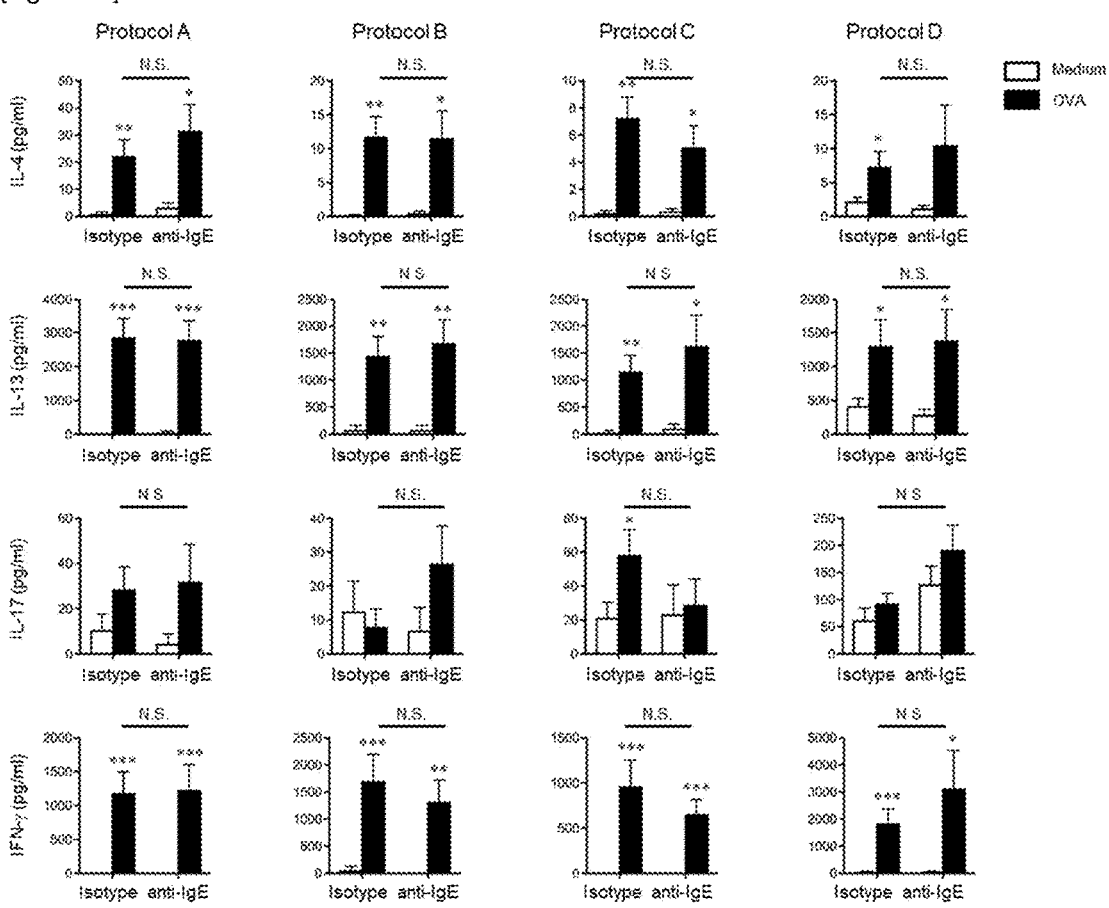

[Figure19]
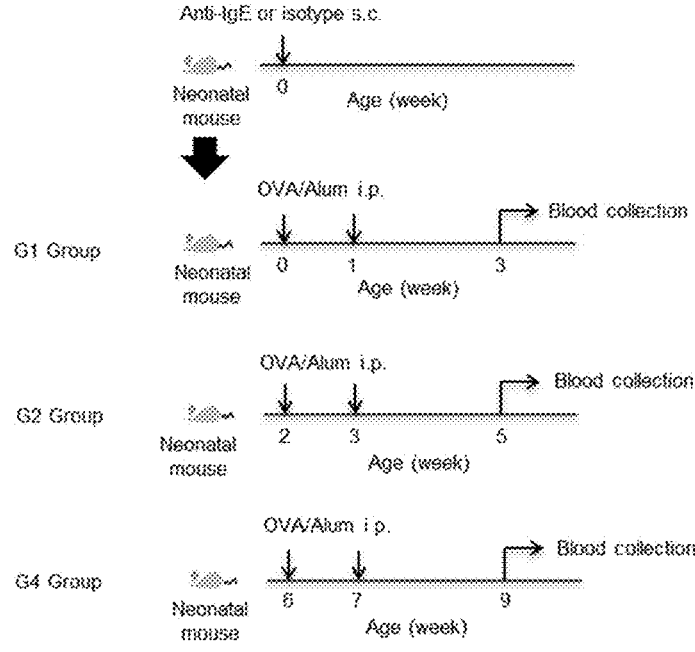
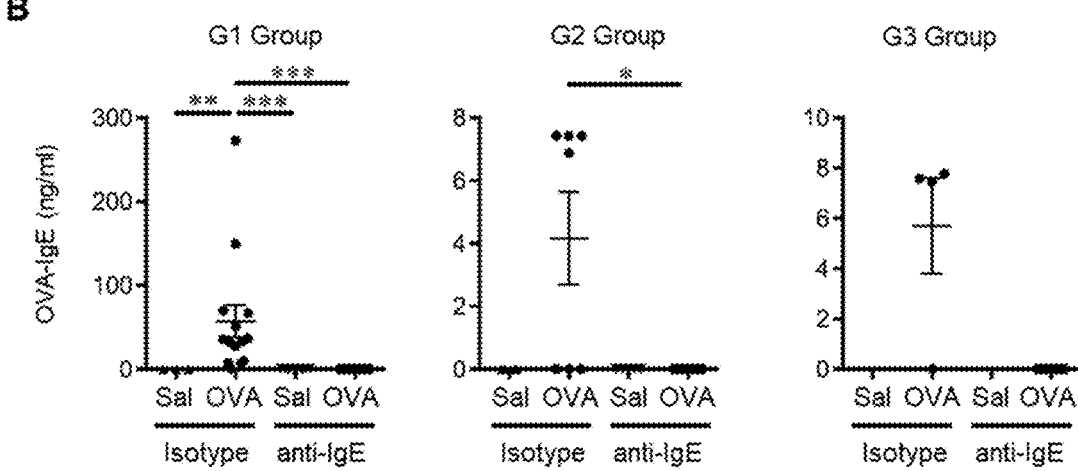

[Figure 20]

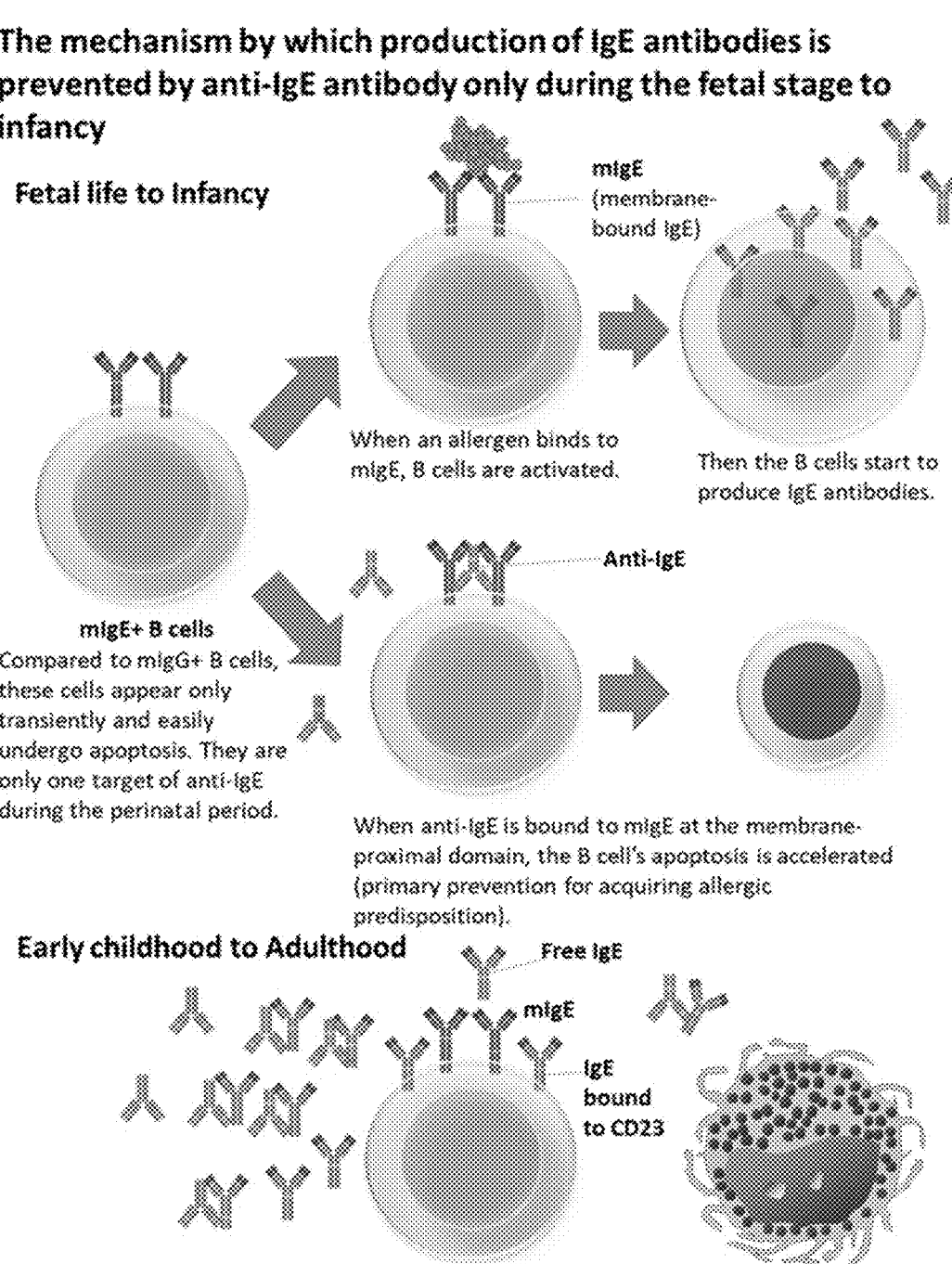

The mechanism by which production of IgE antibodies is prevented by anti-IgE antibody only during the fetal stage to infancy

Fetal life to Infancy mIgE (membrane-bound IgE)

When an allergen binds to mIgE, B cells are activated.

Then the B cells start to produce IgE antibodies.

mIgE+ B cells
Compared to mIgG+ B cells, these cells appear only transiently and easily undergo apoptosis. They are only one target of anti-IgE during the perinatal period.

Anti-IgE

When anti-IgE is bound to mIgE at the membrane-proximal domain, the B cell's apoptosis is accelerated (primary prevention for acquiring allergic predisposition).

Early childhood to Adulthood     Free IgE mIgE

IgE bound to CD23

When anti-IgE is injected to allergic patients, it rarely reaches mIgE. Anti-IgE works clinically mostly by preventing IgE-mediated activation of effector cells (tertiary prevention for exacerbation of symptoms).

METHOD FOR PRIMARY PREVENTION OF ALLERGIC DISORDERS DURING INFANCY THROUGH IgE-CLASS-SPECIFIC IMMUNOSUPPRESSION

TECHNOLOGICAL FIELD

The present disclosure relates to a method for inhibiting the production of IgE antibodies specific to various allergens, comprising preventing acquisition of an allergic predisposition, which starts from early infancy ('early infancy' is defined as one month to four months after birth), by suppressing IgE-class-specific immune responses during the fetal period to infancy as a fundamental method for preventing the onset of allergic disorders.

BACKGROUND ART

Fifty years ago, there were few patients in Japan with allergic disorders, but it is now said that one in three people in the nation has some kind of allergy. Allergies are considered to be closely related to industrialization and civilization, and they have become a major issue in Japan and other developed countries, including European nations and the United States. The following is a summary of the morbidity rates and medical expenses for various allergic disorders, centered on Japan.

Hay Fever

The most common allergic disorder in Japan is hay fever (i.e., seasonal allergic nasal conjunctivitis). The prevalence of Japanese cedar pollinosis increased 2.6 fold from 1980 to 2000, reaching nearly 20% of Japan's population. A survey in Fukui Prefecture in 2006 and 2007 found the prevalence of Japanese cedar pollinosis to be 36.7% of Japan's population. The annual medical cost of Japanese cedar pollinosis, reported in 2000, was estimated to be 286 billion yen in total, including indirect expenses of 60.1 billion yen for absence from work, etc. However, in the case of Japanese cedar pollinosis, in addition to loss of labor/study time (absenteeism) due to the illness, reduced productivity (presenteeism) is also considered to be significant. For example, it is estimated that reduced labor productivity due to antihistamines, which are commonly used over-the-counter medications for Japanese cedar pollinosis, has a cost equivalent to 145 billion yen a month. (The pollen season spans 4 to 6 months, except on the island of Hokkaido.)

Asthma

A survey conducted by the Japanese Ministry of Health, Labor and Welfare in 2011 estimated the number of asthmatic patients visiting medical institutions to be 1,045,000. A 2008 survey using the international common simple questionnaire (International Study of Asthma and Allergies in Childhood: ISAAC) indicated that the prevalence of asthma in childhood (6-7 years of age) in Japan was 19.9%. The prevalence of childhood asthma, using the ISAAC questionnaire is over 20% in the UK, Australia, etc. According to a 1999 survey by the Ministry of Health, Labor and Welfare, the economic burden of medical care for asthma treatment in Japan was estimated to be 451.7 billion yen (the number of asthmatic patients visiting medical institutions totalling 1,196,000; 3.78 billion yen per 10,000 patients). A questionnaire survey of households in the United States (population: 300 million) in 2007 reported that the number of asthmatic patients was 13 million, and the economic burden of medical care for asthma treatment was $56 billion (approximately 5.60 trillion yen) annually, including $5.9 billion for absenteeism, death, etc. (the economic burden of medical treatment was $50.1 billion, or 3.85 billion yen per 10,000 patients, in the US, which is roughly equivalent to that in Japan).

Atopic Dermatitis

The prevalence of atopic dermatitis peaks in early childhood and affects 9.8-13.2% of Japan's population according to a survey based on diagnosis by Japanese physicians. These figures are similarly high as in other industrialized countries. The financial loss due to treatment of atopic dermatitis and reduced labor productivity was reported to be $5.3 billion per year (530 billion yen) in a US survey and 1.5-3.5 billion euros (about 200-460 billion yen) per year in a German (population: 80 million) survey. As in the case of hay fever, allergic skin disorders accompanied by itching, such as atopic dermatitis, contact dermatitis, urticaria, etc., have been shown to have a large negative effect due to decreased labor productivity (presenteeism).

Food Allergies

The prevalence of food allergies varies greatly according to the investigative method. However, there are many reports that the rate in industrialized countries is 2% or so by doctor diagnosis, and it is increasing even in the $21^{st}$ century.

As described above, it is estimated that in Japan the sum of medical expenses for all allergic disorders, including food allergies, and the economic loss relating to absenteeism and decreased labor productivity exceeds at least 1 trillion yen annually. In addition, the impact from presenteeism is likely to be equal to or greater than the loss due to medical expenses and absenteeism.

Drugs for Allergic Disorders

Various anti-allergy agents (chemical mediator release inhibitors, histamine H1 receptor antagonists, thromboxane A2 receptor antagonists, leukotriene receptor antagonists, Th2 cytokine inhibitors, etc.) are used to alleviate the symptoms of allergic disorders. However, they are only symptomatic treatments, not fundamental treatments.

Omalizumab, a humanized anti-human IgE monoclonal antibody, was originally developed as a therapeutic agent for allergic asthma, and it was approved as a therapeutic agent for bronchial asthma in adults in Japan in January 2009 (150 mg preparation) and in September 2012 (75 mg preparation), and as a treatment for bronchial asthma in children in August 2013. As of March 2017, it has been approved as a treatment for allergic asthma in more than 90 countries worldwide and as a treatment for chronic idiopathic urticaria in more than 85 countries worldwide. Although omalizumab has a stronger palliative effect on allergic symptoms compared to the above-mentioned anti-allergy agents, its application to other allergic disorders has not been approved because it is an antibody drug, which is a biological drug, and it is thus much more costly than the anti-allergy agents. Furthermore, at present, omalizumab is also only a symptomatic treatment for allergic asthma and chronic idiopathic urticaria, not a fundamental treatment.

Because the number of patients with allergic disorders is increasing not only in Japan but also worldwide, the economic losses, including medical expenses, are also getting larger year by year worldwide. Moreover, the overall medical costs of treating allergic disorders are expected to increase even further with the spread of biologics and standardization of global medical practices in the future. Therefore, establishment of a method leading to fundamental preventive measures for allergic disorders is an urgent issue.

Prevention of Onset of Allergic Disorders

Most allergic disorders develop in early childhood. Furthermore, it can hardly be expected that an allergic disorder, once developed, will be resolved in adulthood, i.e., it is very unlikely that a patient will become negative for an allergen-specific IgE antibody once it has been acquired. Therefore, it is important to prevent the onset of allergic disorders in infancy. In particular, prevention of development of eczema/atopic dermatitis in infancy up to several months after birth and subsequent sensitization to various allergens is considered to be the key to suppressing the development of 'allergy march' (i.e., the natural history of child allergies, in which individuals with an allergic predisposition develop food allergies and atopic dermatitis in infancy, mite allergy and asthma as young children, and then hay fever and rhinitis as school children). This concept is supported by a report that development of eczema/atopic dermatitis within up to 3-4 months after birth, especially during 1-2 months after birth, correlated strongly with a diagnosis of a food allergy in 3-year-old children (odds ratio: 6.6).

Given that the number of patients with allergic disorders is rapidly increasing, it is expected that, in Japan alone, the medical costs relating to treatment of allergic disorders will run to several trillion yen annually in the coming decades unless a method for preventing the onset of allergic disorders in infancy is established immediately. Thus, various allergy-preventive measures such as skin care and earlier oral intake of allergens have been tried in infants, but to date satisfactory results have been obtained only for certain antigens.

Therefore, there is a strong need to establish fundamental methods for preventing allergic disorders in infants.

SUMMARY OF PRESENT DISCLOSURE

Problems to be Solved

One object of the present disclosure is to provide a method leading to fundamental measures for the prevention of allergic disorders.

Means to Solve the Problem

Summary of Means to Solve the Problem

The inventors of the present disclosure have discovered, as described below, a method for suppressing IgE-class-specific immune responses during infancy (defined as 'one month to 12 months after birth' in this specification) by administration of anti-IgE antibodies in the fetal stage (defined as 'second and third trimesters after conception' in this specification) or at any time during the newborn stage (defined as 'up to one month after birth' in this specification) and infancy. As a result, it can be expected that the onset of various allergic disorders (food allergies (egg allergy, cow's milk allergy, peanut allergy, wheat allergy, etc.), hay fever, atopic dermatitis, asthma, etc., are cited as examples) that occur subsequent to production of allergen-specific IgE antibodies may be efficiently prevented, and that future allergy-related medical expenses may be greatly reduced.

Many individuals with allergic disorders often follow a course in which they first develop atopic dermatitis and a food allergy, and then, after early childhood, they develop asthma and allergic rhinitis. Based on various recent research results, it has been surmised that development of atopic dermatitis (eczema) during infancy causes activation of epidermal Langerhans cells and enhances IgE antibody sensitization, which leads to the onset of allergic disorders such as food allergies. However, it has been learned that even if eczema is present, only the presence of eczema and the living environment for the first several months (3-4 months) after birth correlate strongly with the production of allergen-specific IgE antibodies (so-called acquisition of an allergic predisposition) and the development of food allergy, and that this correlation weakens with age.

Therefore, at least in order to solve the above-mentioned problem, the inventors developed a strategy for preventing the acquisition of an allergic predisposition by completely controlling the production of IgE antibodies for up to 3-4 months after birth. In the present specification, 'allergic predisposition' is defined as being positive for allergen-specific IgE antibodies. And, as a way to realize that strategy, it is hypothesized that when a therapeutic anti-IgE antibody is administered to a pregnant woman, it is transferred to the fetus across the placenta and suppresses the fetal production mechanism of IgE antibodies (i.e., via suppression of E chain mRNA expression, etc.), leading to inhibition of IgE-class-specific immune responses during the newborn and infancy period of the child born to the woman (immunoglobulin E (IgE)-class-specific tolerance or IgE-class-specific immunological tolerance is established). 'Immunological tolerance' generally refers to a lack of or a suppression of a specific immune response to a specific allergen, but in the present specification, 'IgE-class-specific immunological tolerance' is defined as 'a condition in which IgE antibody production against all allergens is lacking or inhibited in an immunoglobulin E (IgE)-class-specific manner.'

At least in order to verify this hypothesis, anti-mouse IgE antibody (IgG1 kappa antibody, which is the same isotype as omalizumab) or control antibody was administered twice (mid- and late-pregnancy) to pregnant C57BL/6 mice, and from 0, 2, 4 or 6 weeks after birth the offspring were sensitized twice with OVA (ovalbumin). Then the effects on the offspring's production of OVA-specific IgE antibodies were examined. As a result, when offspring were sensitized with OVA at any of 0, 2, 4 and 6 weeks after birth, a marked increase in the OVA-specific IgE antibody titer was observed in offspring born to mice administered with the control antibody, but there was no increase in the titer in the offspring of mice administered with the anti-mouse IgE antibody. Interestingly, administration of the anti-mouse IgE antibody did not affect production of OVA-specific IgG1 antibodies.

Furthermore, in an evaluation system using newborn C57BL/6 mice, it was found that even when anti-mouse IgE antibody was administered to the newborn mice, the production of allergen-specific IgE antibodies could be selectively inhibited for at least 6 weeks, which is similar to the case of its administration to pregnant mice.

Because the half-lives of mouse and human IgG antibodies are 6-8 days and 22-23 days, respectively, an age of 6 weeks in mice can be considered equivalent to an age of about 3-4 months in humans when converted on the basis of the half-life of IgG. Therefore, there is a strong possibility that the goal of completely suppressing IgE antibody production for up to about 3-4 months after the birth of human babies can be achieved.

Because it was reported that mice with IgE-class-specific deficiency have no distinct abnormalities, including of their phenotypes, it can be surmised that there is a strong possibility that complete suppression of IgE antibody production in human infants for about 3-4 months after birth will not have adverse effects.

Omalizumab, the anti-IgE antibody that is widely used for intractable allergic disorders such as asthma in humans, ameliorates the symptoms of allergic disorders by the mechanism of neutralizing free IgE antibodies in the blood, has few adverse effects, and has been safely administered to pregnant women. In addition, an in vitro study found that when B cells expressing IgE as a membrane receptor (mIgE+ B cells) due to forced stimulation with interleukin 4 (IL-4) and clusters of differentiation 40 ligand (CD40L) were exposed to omalizumab, the cells became anergic or apoptotic.

Taken together, the above findings revealed that when omalizumab is administered to pregnant women with severe allergic disorders (their children are high-risk) in the third trimester, or to children born to such pregnant women at any point from the newborn stage to early infancy, there is a strong possibility that the production of allergen-specific IgE antibodies will be markedly suppressed for about 3-4 months after birth, i.e., acquisition of an allergic predisposition will be prevented. The present disclosure has been accomplished at least based on the above embodiments.

Detailed Explanation of the Method for Solving the Problem

I. Findings Regarding the Onset of Allergies
New Concept on Food Allergy: Dual Allergen Exposure Hypothesis
Percutaneous Sensitization and Food Allergy Food allergies had conventionally been considered to develop through intestinal sensitization, but in recent years the importance of percutaneous sensitization has become clear, and the concept of the mechanism of development of food allergies is changing.

Food allergies manifest most commonly in infancy (about 10%), and in many cases atopic dermatitis is present as a complication. In particular, it had been known that the earlier the onset of atopic dermatitis in infancy and the greater its severity, the more readily food allergy develops as a complication; however, elucidation of the pathologic condition linking the two disorders was not easy.

Based on the premise that food allergies develop through oral intake, since 2000 the American Academy of Pediatrics has recommended that for high-risk children born to parents with allergic disorders, various foods, including peanuts and eggs, should be avoided during pregnancy/lactation and throughout infancy and early childhood. A number of epidemiological surveys were conducted to verify the preventive effects of such dietary restrictions, but all of them generated only negative results.

On the other hand, percutaneous sensitization has been drawing attention as a new risk.

In 2003, Lack et al., UK pediatricians, conducted a cohort study and found that among baby oil skin care products in widespread use for moisturizing the skin of infants in the UK, peanut oil-containing products placed infants at risk of peanut allergy.

In 2006, filaggrin (FLG) loss-of-function gene mutations were reported to play a role in the development of atopic dermatitis and allergy march. Based on accumulating evidence supporting such a relationship between the skin barrier and allergic disorders, in 2008, Lack proposed a novel hypothesis called the 'dual allergen exposure hypothesis'. This hypothesized that oral exposure induces an inherent immune tolerance, whereas allergic sensitization is largely caused by percutaneous exposure. This dual allergen exposure hypothesis is supported by the following studies.

Studies of peanut allergy found that its prevalence was lower in the Philippines and Israel, where peanuts are freely ingested during infancy, than in the US and UK, where restriction of intake of peanuts was recommended for the weaning period. Furthermore, another study revealed that heavy peanut consumption by a child's family placed the child at greater allergy risk than the child's own peanut intake, i.e., children can be sensitized to food allergens as environmental allergens.

In Japan, wheat allergy developed in users of soaps called tea drip soaps that contain wheat components (hydrolyzed wheat), and this became a societal problem. This was the first case in which it was clinically proven that percutaneous exposure can induce food allergies.

Furthermore, it has been found that when there is disruption of the epidermal barrier, a food allergy due to percutaneous sensitization can develop due to repeated exposure to food allergens, even when the food components are not processed. That is, food allergies may develop when a housewife or a cook handles food with his/her bare hands with rough/broken skin, or when cosmetic treatment is performed using a skin care product containing a food component.

Thus, while evidence is accumulating regarding the development of food allergies via percutaneous sensitization, there is increasing expectation that proper skin care will have a preventive effect on development of food allergies.
Mechanism of Action of Percutaneous Sensitization
Structure of the Skin Barrier The skin covering the outer surface of the body not only functions as a barrier that forms the boundary between the external world and the living body, but also monitors for barrier damage and invading foreign substances. The structure of the skin is divided inward into three layers, i.e., the epidermis, the dermis and the subcutaneous tissue, and the outermost epidermal layer is further divided inward into four layers, i.e., the stratum corneum, the stratum granulosum, the stratum spinosum and the stratum basale. Keratinocytes comprise 95% of the epidermal volume. The skin barrier consists mainly of the stratum corneum and tight junctions of the stratum granulosum.

The stratum corneum is the barrier that separates the body from the atmosphere, and it physically protects the body from damage caused by dryness or external force.

In the stratum granulosum, tight junctions exist between cells, and it divides the extracellular fluid environment of the epidermis into two compartments, the surface side and the inner side of the tight junction barrier. And, in the stratum spinosum on the inner side of the tight junction barrier, epidermal dendritic cells (Langerhans cells) monitor antigens that may invade due to damage to the epidermal barrier.
Congenital Skin Barrier Disorders and Allergy Recently, genetic abnormalities of skin barrier components have been identified in some patients who present with a clinical picture similar to atopic dermatitis. In Netherton's syndrome due to insufficiency of the serine protease inhibitor LEKTI encoded by the SPINK5 gene and in peeling skin syndrome type B in which corneodesmosin, a substrate for KLK5, is completely defective, an atopic dermatitis-like rash appears early after birth, and features such as IgE elevation and elevation of food allergen-specific IgE antibodies are observed. Although a relationship between atopic dermatitis and a single nucleotide polymorphism of the claudin-1 gene, which is the adhesion molecule of tight junctions, was also reported, a filaggrin (FLG) gene mutation was found to show the strongest correlation with atopic dermatitis.

Palmer et al. reported that FLG gene mutations are associated with the development of atopic dermatitis (20). FLG gene mutations differ among races and are detected in approximately 27% of Japanese patients with atopic dermatitis. It was revealed that atopic dermatitis patients with FLG gene mutations developed atopic dermatitis early in infancy, had high IgE levels, developed food allergies as a complication and were at high risk of developing asthma. Interestingly, it was clarified that in FLG-deficient mice, skin inflammation did not occur in a specific pathogen free (SPF) environment, but IgE elevation and skin inflammation first developed due to percutaneous sensitization. It was reported that eczema/atopic dermatitis that developed up to 3-4 months after birth, especially during 1-2 months after birth, correlated strongly with a diagnosis of food allergy in 3-year-old children (odds ratio: 6.6). Also, the risk that infants who are positive for egg antigen-specific IgE antibody at 1 year of age will become positive for mite antigen-specific IgE antibody by 3 years of age was reported to be 27 fold compared to non-positive infants. These findings suggest that percutaneous sensitization to a food, which is often the first sensitizing antigen in humans, is a risk not only for development of dermatitis and food allergy, but also a risk of later development of asthma and rhinitis, and it is an important trigger that induces allergy march.

Skin Barrier Disorders and Percutaneous Sensitization

The mechanism by which percutaneous sensitization to food antigens occurs via skin barrier disorders is thought to be as follows. Normally, molecules larger than 500 Daltons cannot pass through healthy skin, but when the stratum corneum barrier is impaired, food antigens, which are several tens of kilodaltons, are taken up intracutaneously. This does not just mean that the antigens pass through the broken barrier. Cytokines such as IL-1 (interleukin 1), TNF-α (tumor necrosis factor α) and TSLP (thymic stromal lymphopoietin) are produced by keratinocytes that are activated by various signals from the epidermis, and Langerhans cells activated by those cytokines actively take up the antigens.

Langerhans cells are present inside the tight junctions in the epidermis, but once activated, they extend their dendritic tips beyond the tight junction barrier to just below the stratum corneum and take up antigens via the tips. Langerhans cells that have taken up antigens then migrate to the regional lymph nodes in response to TSLP, which is considered to be the master switch for the Th2 (T helper 2) response, where they induce differentiation/proliferation of Th2 cells and production of IL-4 and IgE antibodies.

Thus, in skin placed under a Th2 environment, the expression of skin barrier components is further reduced, and the barrier function is further impaired. Moreover, if a Th2 allergy is strongly induced, the barriers of other organs are also placed under a Th2 environment, and it is thought that food allergy, asthma and rhinitis occur in succession. In the intestinal mucosa, which is closely linked to food allergies, elevation of the IgE antibody and Th2 cytokine concentrations can cause the number of mast cells to increase; their degranulation causes tight junction damage that leads to enhanced intestinal permeability, which is thought to promote allergic inflammation and sensitization of the intestinal mucosa.

For causation of percutaneous sensitization, it is important that the stratum corneum is the level at which external skin damage occurs due to degreasing with acetone, shaving with a razor, etc. Furthermore, acquired barrier disorders resulting from excessive use of soap (surfactant), a low humidity environment due to air conditioning, the action of proteases contained in mites and pollen, etc., in the environment, scratching, etc., are required to cause percutaneous sensitization. These findings indicate that preventing disorders of the stratum corneum and acquired barrier disorders of the skin due to a low humidity environment, etc., helps prevent percutaneous sensitization, and for that reason it can be expected that proper skin care will have a preventive effect on the onset of food allergies.

Conventional Strategies for Preventing Onset of Allergies, Including Food Allergies Prevention of Percutaneous (Due to Eczema) Sensitization Among allergic disorders, atopic dermatitis develops within several months after birth. A recent study showed that the presence of atopic dermatitis in infancy is a risk factor for development of food allergies. A defect in the gene for the barrier function protein, filaggrin, which is present in the epidermis but not in the airway epithelium, is a risk factor not only for atopic dermatitis and food allergies, but also for hay fever and asthma. In other words, it can be said that the starting point of the allergy march is the presence of atopic dermatitis in infancy.

Based on the dual allergen exposure hypothesis, the onset of food allergies should be able to be prevented if percutaneous sensitization can be prevented and oral immune tolerance can be effectively induced. From this viewpoint, studies have examined whether percutaneous sensitization and, eventually, development of other allergic disorders can be obviated by preventing the onset of atopic dermatitis by using a skin moisturizer or the like.

Randomized controlled trials using moisturizers conducted in Japan and by a UK/US group found that application of a moisturizer beginning from the newborn stage significantly prevented the onset of atopic dermatitis and that onset of atopic dermatitis was associated with egg white antigen sensitization. In more detail, at the Japanese National Center for Child Health and Development, in 2014, skin care with a moisturizer was started within one week after birth and continued for 32 weeks in high-risk children whose parents and/or siblings had a history of atopic dermatitis; at the end of the treatment, the development of atopic dermatitis and allergen sensitization were evaluated. It was found that although daily application of a moisturizer reduced the onset of atopic dermatitis (eczema) by about 32%, there was no significant reduction in food allergen sensitization. However, comparing the group that did not develop atopic dermatitis with the group that developed atopic dermatitis during the course of the trial, food allergen sensitization was significantly inhibited in the former, which suggests that the skin care had an indirect effect.

At present, based on the above evidence, it has been suggested that complementing and maintaining the skin barrier by good skin care may help to prevent the onset of atopic dermatitis and also to prevent percutaneous sensitization.

Prevention of Sensitization by Allergen Elimination

The amount of mite allergen in household dust such as bedding correlates with the frequency of asthma attacks. The frequency of peanut allergy is high in the United States where peanut consumption is high. In recent years, a major cause of the increase in cedar pollinosis in Japan is that the cedar trees planted in the post-WWII period reached the age at which they scatter a lot of pollen. Thus, it is clear that an increase in the amounts of allergens is a contributory cause to the increase in allergic disorders.

When the responsible allergen is determined after onset of an allergic disorder, the basic treatment policy for prevention of expression/exacerbation (tertiary prevention) of the symptoms of the allergic disorder is to eliminate the causal allergen.

However, various intervention studies conducted to date have failed to prove the onset-preventive effect (primary prevention, secondary prevention) of allergen elimination prior to infancy. Conversely, it was reported that in the United States, where peanut allergen levels in the environment are high, peanut intake restriction in infancy increased the risk of peanut allergy.

Based on the above evidence, it has become clear that it is important not to delay the start of oral intake due to a high genetic risk. In addition, it is considered unrealistic to prevent sensitization by mites, cedar pollen, food allergens, etc., which are universally present in the environment, by means of antigen elimination.

Induction of Tolerance (Immune Tolerance) by Antigen Transfer

Even if the allergen is the same, depending on its route of invasion, IgE antibody production may be suppressed. When allergens invade via the inflamed skin of atopic dermatitis or the airway mucous membranes of asthma patients, sensitized mast cells are activated and cytokines released from epithelial mesenchymal tissue enhance the production of IgE antibodies. However, it is thought that because healthy sublingual and intestinal tracts are environments where regulatory T cells are readily generated, those cells are generated when allergens invade, and that when the host is naïve to the allergens because of infancy, etc., immune tolerance is established; also, even when the host has already developed an allergic disorder, tolerance is induced because harmless IgG antibodies that do not cause allergic reactions are produced.

Therefore, clinical trials have been conducted to prevent the onset of food allergies.

In 2015, Lack et al. published new evidence generated in a randomized controlled trial showing that it would be beneficial for even high-risk children to consume peanuts as early as possible, rather than delaying the start of intake. When high-risk infants started peanut consumption at 4-11 months of age, the onset of peanut allergy by 5 years of age was reduced by 11-25% in absolute value and by 80% relatively compared to the avoidance group. With regard to eggs, the most common allergy-causing food in many countries, a clinical intervention trial conducted by Japan's National Center for Child Health and Development found that the onset of egg allergy by 1 year of age in children who ingested chicken eggs from 4 months after birth was reduced by 80% compared to the children in the placebo group. It is noteworthy that, in this trial, unlike the conventional method, as the intervention method hard boiled egg was gradually increased from a small initial amount, and early treatment for eczema was uniformly performed.

As described above, studies have indicated that oral intake of allergy-causing substances such as peanuts and chicken eggs from the early stage of weaning is effective in suppressing the onset of allergic disorders such as food allergies.

Hygiene Hypothesis

Based on the results of many epidemiological surveys, it was reported that when people grow up in rural areas with high endotoxin levels in the environment or in unsanitary areas, their subsequent incidence of hay fever and their positive rate for allergen-specific IgE antibody are reduced.

Immunologically, it is surmised that Th1 cells, which antagonize Th2 cells, increase under unsanitary conditions. That is, when allergens such as mite antigens invade for the first time after birth, they are taken up by antigen-presenting cells, which then present the allergens to naive T cells in regional lymph nodes. At this time, when Toll-like receptors (TLRs)—which are located on antigen-presenting cells and recognize molecules such as endotoxin that are derived from bacteria and viruses—are simultaneously stimulated, the naïve T cells do not differentiate into Th2 cells, and instead Th1 cells are generated. The allergen-specific Th1 cells do not promote production of IgE antibodies and cause no pathological reactions. This is the current immunological explanation.

As the rationale for the hygiene hypothesis, it was recently reported that an endotoxin in the environment causes expression of A20 protein (Tnfaip3) on airway epithelial cells, which inhibits activation of dendritic cells (Langerhans cells). This could be an important strategy for preventing the onset of some asthma and pollinosis cases that are not caused by percutaneous sensitization.

Proposal of Fundamental Measures for Infant Allergies

Based on the above evidence, it has been suggested that early intervention in infant eczema and oral intake of allergy-causing substances from the early weaning stage are effective in preventing the onset of allergic disorders such as food allergies. On the other hand, use of a moisturizing agent was not observed to suppress food (chicken egg) antigen sensitization, whereas ingesting cooked chicken eggs and peanuts from the early weaning stage was able to prevent the onset of these allergies. However, a suppressive effect has not been proven for other allergens. Therefore, it is necessary to establish a safer and more efficient means for preventing the onset of asthma and other allergic disorders, a method that can be expected to have an effect sufficient to reduce future medical costs.

The present inventors focused on the IgE antibody, which is the most important causative molecule of type I allergies, in order to design a safer and more surefire method for allergy prevention. Many individuals with allergic disorders often follow a course of developing atopic dermatitis and food allergies in infancy, followed by developing asthma and allergic rhinitis from early childhood. Based on various recent research results, it is now thought that atopic dermatitis (eczema) develops first, which then leads to epidermal Langerhans cell activation, enhanced IgE antibody sensitization and onset of allergic disorders such as food allergies. However, even if eczema is present, only the presence of eczema and the living environment for the first several months (3-4 months) after birth correlate strongly with the production of allergen-specific IgE antibodies (so-called acquisition of an allergic predisposition) and the onset of food allergy, and this correlation subsequently weakens with age. Taking the above-mentioned findings together, the inventors developed a strategy for preventing acquisition of an allergic predisposition by controlling production of IgE antibodies for up to about 3-4 months after birth. 'Allergic predisposition' in the present specification is defined as being positive for an allergen-specific IgE antibody. As a way to realize the strategy, it is hypothesized that when a therapeutic anti-IgE antibody is administered to a pregnant woman, it is transferred to the fetus across the placenta and suppresses the fetal production mechanism for IgE antibodies (i.e., via suppression of E chain mRNA expression, etc.), leading to inhibition of IgE-class-specific immune responses during the newborn and infancy periods of the child born to the woman (IgE (immunoglobulin E)-class-specific tolerance or IgE-class-specific immunological tolerance is established). Here, 'immunological tolerance' generally refers to a lack of or suppression of a specific immune response to a specific allergen, but in the present specification, 'IgE-class-specific immunological tolerance' is defined as a condition in which [IgE antibody production against all allergens is lacking or inhibited in an IgE (immunoglobulin E)-class-specific manner.

The present inventors verified this hypothesis by experiments in which an anti-mouse IgE antibody was administered to pregnant mice and neonatal mice, and the results showed that a method for preventing IgE-class-specific immune responses from the fetal stage to infancy was successful.

Humanized Anti-IgE Antibody

Since IgE was discovered by Ishizaka et al. in 1966, research on allergies, which had been chaotic, has progressed dramatically together with advances in immunology.

IgE, like IgG, is composed of two heavy chains (H chains) and two light chains (L chains), whereas its constant domain (C domain) is composed of 4 domains in contrast to the 3 domains of IgG, and its molecular weight is 190 kDa versus 150 kDa for IgG. In addition, the binding of IgE to IgE receptors, both the high-affinity FcεRI and the low-affinity FcεRII, occurs at the third C domain, Cε3.

IgE is attached to FcεRI on the surface of mast cells, and when it binds to the corresponding antigen, the mast cells produce and release chemical mediators and cytokines.

Omalizumab is a humanized anti-human IgE antibody that was developed by Genentech Inc. in the US in 1991. Based on a mouse monoclonal antibody with specificity for Cε3 of the human IgE molecule, this antibody is produced by genetic recombination technology so that only the binding site specific for human IgE Cε3 is left, and the remaining 95% is replaced with the molecular structure of human IgG1K.

Genentech, Inc. has filed a number of patents related to omalizumab: U.S. Pat. No. 6,685,939 (Method of preventing the onset of allergic disorders), and Japanese Patent 345792 (Immunoglobulins for specific Fc epsilon receptors). The summaries of the inventions of those patents are presented below.

Overview of Genentech's Patented Invention

"We have identified domains and specific residues of IgE which play an important role in binding IgE to its FCEL and FCEH receptors, and based on this information we have designed polypeptides which remain capable of substantially binding to only one of these receptors while being substantially incapable of binding to the other of the receptors. These polypeptides are referred to as differential binding polypeptides. The differential binding polypeptides of this invention are useful in diagnostic procedures for IgE receptors or in the therapy of IgE-mediated disorders such as allergies. They are also useful in preparing antibodies capable of binding regions of IgE that participate in receptor binding. In an embodiment we provide antibodies which are capable of binding FCEL-bound IgE but which are substantially incapable of binding FCEH-bound IgE. In another embodiment of this invention, variant anti-IgE antibodies are provided for use in diagnosis or for the therapy or prophylaxis of allergies and other IgE-mediated disorders."

"The FCEH and FCEL-specific polypeptides and anti-IgE antibodies (especially those with reduced immunogenicity) are useful in therapies for the treatment or prophylaxis of allergies, although the FCEH specific polypeptide subgroup which bears cytotoxic functionalities is not considered suitable for therapy since it could lead to degranulation of mast cells and basophils. Otherwise, the polypeptides typically are administered to a patient who is known to be sensitized to an allergen, preferably to an acute allergic response."

Clinical Effect of Humanized Anti-Human IgE Antibody, Omalizumab

Omalizumab blocks the binding of IgE to FcεRI on the surface of mast cells and basophils by binding to Cε3 of IgE. As a result, it is thought that even if antigen exposure occurs, the series of reactions of mast cells and basophils via IgE are blocked, thereby inhibiting development of symptoms such as asthma due to allergic reactions.

When the effects of anti-IgE antibody therapy on antigen-induced asthmatic reactions were examined, immediate and delayed reactions were significantly suppressed. Omalizumab therapy has been positioned in the guidelines as a new treatment for intractable allergic asthma. In addition, the efficacy and safety of omalizumab were confirmed in studies on childhood asthma and large-scale post-marketing surveillance, and it was also approved for childhood bronchial asthma. Furthermore, omalizumab has been approved as a treatment for idiopathic urticaria. In the future, if it becomes possible to lower the drug price of the preparation, it can be expected that the indications for omalizumab may be expanded to include intractable allergic rhinitis and dermatitis, as well as combined use with antigen-specific hyposensitization therapy. In any case, because anti-IgE antibody therapy is one of the fundamental therapeutic methods based on the elucidation of the pathological mechanism of allergic disorders such as asthma, further expansion can be expected in the future.

Regarding the Safety and Tolerability of Omalizumab

Because the antibody-dependent cellular cytotoxicity of omalizumab is low, even if it is administered to an adult who already has allergen-specific IgE antibodies or memory B cells, the serum IgE antibody titer does not decrease. However, in vitro experiments found that omalizumab reacted with membrane-bound IgE on B cells and reduced the amount of IgE antibody produced by B cells by suppressing expression of ε-chain mRNA (52, 53).

Because omalizumab does not react with IgE that has already adhered to mast cells or basophils via FcεRI, it is thought that there is no concern of causing an allergic reaction by crosslinking. Furthermore, in its reaction with free IgE molecules that are not bound to receptors, omalizumab forms IgE-omalizumab immune complexes. Because these immune complexes are small in amount, soluble and have no complement-binding ability, it is thought that there is no fear of causing serum disorder, although the risk of cardiovascular disease and cerebrovascular disease may be slightly increased.

Anaphylaxis

Because omalizumab is not a fully human antibody, there is a possibility that shock and anaphylaxis might occur due to production of antibodies against the amino acid sequence and antigen recognition site of the remaining mouse portion, but the frequency of such events is extremely low at 0.2% or less, as shown below. Although shock and anaphylaxis caused by omalizumab administration have not been observed in clinical trials in Japan, in overseas adult clinical trials in bronchial asthma patients, anaphylaxis/anaphylaxis-like reactions were observed in 0.13% (7/5367 cases) of the omalizumab group and in 0.03% (1/3087 cases) of the control group, including a placebo. Thus, although the incidence was low, it tended to be higher in the group treated with the drug. Furthermore, in an overseas pediatric clinical trial in bronchial asthma patients, anaphylaxis/anaphylaxis-like reactions were observed in 0.2% (1/624 cases) of the drug group and in 0.3% (1/302 cases) of the placebo group. Overseas spontaneous post-marketing reports show that events reported as anaphylaxis, and hypersensitivity reactions that were not reported as anaphylaxis but may in fact have been anaphylaxis, were observed in 124 people, and the frequency calculated based on the estimated number of patients prescribed this drug (about 57,300 patients) was 0.2%. It should be emphasized here that the frequency of reports of anaphylaxis related to omalizumab administration is lower than the frequencies associated with the administration of other biologics used in other applications.

In addition, serum disease or serum disease-like syndrome was not observed as a side effect in any of the administration groups. Moreover, none of the patients in the omalizumab administration groups produced anti-omalizumab antibodies.

Parasitic Infections

Omalizumab forms complexes with free IgE, thereby reducing free IgE. Because IgE is thought to be one of the factors related to host defense against parasitic infections, there is a theoretical possibility that susceptibility to parasitic infections is increased by omalizumab treatment. In order to assess that risk, a 52-week, randomized, double-blind, placebo-controlled clinical trial of omalizumab was conducted in 137 patients with asthma or rhinitis who were at high risk of intestinal parasite infection. That 1-year clinical trial found no significant increase in the risk of parasitic infection and no difference in the response to antiparasitic therapy in the omalizumab group compared to the control group.

Thrombocytopenia

In a non-clinical study, when omalizumab was administered to cynomolgus monkeys at doses of 3.7-20 times the maximum dose for humans, a decrease in the platelet count was observed. Therefore, the clinical trial and post-marketing survey data were analyzed, but no effect of omalizumab on platelets was observed.

Malignant Neoplasia

Analyses were conducted for malignant neoplasia for all indications in the 35 omalizumab clinical trials. Malignant neoplasms were reported in 25 (0.50%) of the 5015 patients treated with omalizumab and in 5 (0.18%) of 2845 subjects in the control groups. All the malignant neoplasms were solid tumors except for one in the omalizumab group.

The incidence of neoplasms in the omalizumab group was similar to that in the general population when comparison was conducted using the NIH SEER database, showing that omalizumab does not significantly increase the incidence of neoplasms. Furthermore, the results of a post-marketing prospective observational cohort study (EXCELS) of omalizumab showed that omalizumab therapy did not increase the risk of developing tumors.

Laboratory Test Values

Omalizumab administration had no impact on the clinical laboratory values for the hemoglobin level, white blood cell count, platelet count, renal function or liver function.

CONCLUSION

A number of clinical trials have shown that omalizumab add-on therapy is clinically useful for patients with moderate to severe or severe persistent allergic asthma.

Overall consideration of the safety data in those clinical trials and the results of clinical trials on concerns specific to omalizumab showed that omalizumab add-on therapy is effective and well-tolerated by patients with moderate to severe or severe allergic asthma.

Regarding the Safety of Omalizumab Administration to Pregnant Women

The Case of Discontinuing Administration of Omalizumab when Pregnancy is Known

During the clinical trials, pregnancy was reported by 47 people, including people whose spouses were receiving omalizumab therapy at the time of conception. Among them, 27 were in the omalizumab treatment group, 18 were in the control group, and the other 2 were women whose spouses were receiving omalizumab therapy. In the omalizumab group (27 patients), 17 patients gave normal birth, 4 underwent elective termination, and 6 experienced spontaneous abortions after stopping administration of omalizumab when the pregnancy became known. In the omalizumab non-administration (control) group (18), 8 gave normal birth, 1 underwent elective termination, 6 experienced spontaneous abortions, and the outcome was unknown for 3. The two women whose spouses were receiving omalizumab therapy at conception gave normal birth. These results indicate that stopping omalizumab treatment when pregnancy is known does not lead to adverse consequences.

Expect: Safety of Omalizumab Administration During Pregnancy

The omalizumab pregnancy registry, EXPECT, is a post-marketing prospective observational study being planned by the US FDA to evaluate the maternal, pregnancy and infant outcomes after exposure to omalizumab, including the incidence of congenital anomalies. EXPECT follows pregnant women who were exposed to omalizumab one or more times within 8 weeks prior to conception or at any time during pregnancy, with data collected at enrollment, first trimester, second trimester, third trimester, birth and every six months up to 18 months post-delivery. Of 169 pregnancies with known outcomes (median exposure during pregnancy: 8.8 months), there were 156 live births of 160 infants (4 sets of twins), 1 fetal death/stillbirth, 11 spontaneous abortions, and 1 elective termination. Among 152 singleton infants, 22 (14.5%) were born prematurely. Of 147 singleton infants with weight data, 16 (10.9%) were small for gestational age. Among 125 singleton full-term infants, 4 (3.2%) had low birth weights. Seven (4.4%) of the infants who had congenital anomalies had major defects, but no pattern of anomalies was observed. The above results reveal that, compared to the data for the general asthma population, the prevalence of major congenital anomalies observed in EXPECT is not higher, and omalizumab does not increase the risk of premature birth or small for gestational age.

Transfer of Omalizumab from Mother to Fetus

The neonatal Fc receptor for IgG (FcRn) is known to play a role in the transfer of IgG from mother to fetus, and in humans, IgG1 and IgG4 are the most easily transferred. Because omalizumab is an IgG1 kappa antibody (49), it is thought that it is transferred into the fetal body when it is administered to a pregnant woman. In fact, in animal experiments using cynomolgus monkeys, placental transfer of omalizumab was observed, while there was no maternal toxicity, fetal toxicity or teratogenicity. In a 2009 review, Corren et al. reported that omalizumab did not adversely affect 27 patients who became pregnant during treatment and were discontinued after the pregnancy was known. In addition, the EXPECT study found no increase in the prevalence of major congenital anomalies and no increase in the risk for premature birth or small for gestational age of the offspring of pregnant women receiving omalizumab during pregnancy compared to the data for the general asthma population. Furthermore, even when pregnant women suffering from chronic idiopathic urticaria received omalizumab during pregnancy, their births were normal and their children developed without physical or mental abnormalities.

With regard to the relationship between lactation and omalizumab, transfer of omalizumab to breast milk has been reported in experiments using cynomolgus monkeys. IgG is transferred from serum to breast milk by the action of FcRn, and it is absorbed from an infant's intestinal tract. In addition, because antigen-IgG complexes are also transported by FcRn, it can be thought that at least some of the IgE-omalizumab complexes are also transferred to breast milk. Although there has been no clarification of any possible effects of omalizumab in breast milk on newborns, an overview of the results of case reports suggests that there may be no serious effects. However, it is needless to say that further studies would be necessary because the number of cases is very small.

The US FDA has classified omalizumab in category B in the fetal risk classification (Although risk to the fetus was not found in animal studies, no human controlled trial has been conducted in pregnant women; or, although adverse effects have been proven in animal studies, the existence of risk has not been corroborated in human controlled studies). Taking together the above reports relating to pregnant women, although it is thought that there is a strong possibility that omalizumab can be safely used during pregnancy, administration of omalizumab to pregnant women is not recommended in the guidelines of any country, and it is thus important to administer it only after weighing the risks/benefits of its use in a pregnant woman (66).

THE PRESENT DISCLOSURE

In Japan, few patients had allergic disorders 50 years ago, but it is now said that one in three people in the nation has some kind of allergy. Allergies are considered to be closely related to industrialization and civilization, and they have become a major issue in Japan and other developed regions such as Europe and the United States. Most allergic disorders develop in early childhood. The underlying acquisition of an allergic predisposition, i.e., the production of IgE antibodies that recognize a specific allergen, starts in the neonatal period to early infancy. It might be theorized that allergic disorders could be prevented by abandoning modern civilization, but that is not a realistic option because infant mortality would likely become as bad as it was before modernization.

As will be described below, the inventors of the present disclosure found a way to suppress the immune response in infancy in an IgE-class-specific fashion by administration of anti-IgE antibodies to pregnant mothers or to their offspring at any time from after birth to infancy. As a result, it can be expected that the onset of various allergic disorders due to the production of IgE antibodies specific to various allergens can be efficiently prevented and that future medical costs will be significantly reduced.

The inventors of the present disclosure discovered a method for preventing allergic disorders, comprising administration of anti-IgE antibodies to a pregnant woman, wherein a production of IgE antibodies is suppressed in the offspring of the woman for up to about 3-4 months after birth, resulting in prevention of subsequent acquisition of an allergic predisposition. When a therapeutic anti-IgE antibody is administered to a pregnant woman, it is transferred to the fetus across the placenta and suppresses the fetal production mechanism for IgE antibodies (i.e., via suppression of E chain mRNA expression, etc.), leading to inhibition of IgE-class-specific immune responses during the newborn and infancy periods of the child born to the woman (IgE (immunoglobulin E)-class-specific tolerance or IgE-class-specific immunological tolerance is established). Furthermore, it was also found that similar results were obtained when the therapeutic anti-IgE antibody was administered to neonates.

The gist of the present disclosure is as follows.
(1) A pharmaceutical composition comprising an anti-IgE antibody that suppresses the production of allergen-specific IgE antibodies in infancy, which is accomplished by administration of said pharmaceutical composition to a pregnant mother and/or a child at any point from after birth to infancy.
(2) A pharmaceutical composition comprising an anti-IgE antibody for suppressing IgE-class-specific immune responses during the fetal stage to infancy is accomplished by administration of said pharmaceutical composition to a pregnant mother and/or a child at any point from after birth to infancy.
(3) A pharmaceutical composition, which is described in (1) and (2), that prevents the onset of allergic disorders in infancy and later.
(4) A combination therapy comprising administration of a pharmaceutical composition containing an anti-IgE antibody and immunotherapy that administers an allergen to the child in order to suppress the production of allergen-specific IgE antibodies in infancy, which is accomplished by administration of said pharmaceutical composition to a pregnant mother and/or a child at any point from after birth to infancy.
(5) A combination therapy comprising administration of a pharmaceutical composition containing an anti-IgE antibody and immunotherapy that administers an allergen to the child in order to suppress IgE-class-specific immune responses during the fetal stage to infancy, which is accomplished by administration of said pharmaceutical composition to a pregnant mother and/or a child at any point from after birth to infancy.
(6) A combination therapy according to (4) and (5), further comprising preventing the onset of allergic disorders in infancy and later.
(7) A pharmaceutical composition comprising a therapeutic antibody for preventing the onset of diseases in infancy and later, which is accomplished by administration of said pharmaceutical composition to a pregnant mother and/or a child at any point from after birth to infancy.
(8) A method for suppressing production of allergen-specific IgE antibodies in infancy, comprising administration of an anti-IgE antibody at a pharmaceutically effective dose to a pregnant mother and/or a child at any point from after birth to infancy.
(9) A method of suppressing IgE-class-specific immune responses during the fetal stage to infancy, which includes administration of an anti-IgE antibody at a pharmaceutically effective dose to a pregnant mother and/or a child at any point from after birth to infancy.
(10) The method according to (8) and (9), further comprising preventing the onset of allergic disorders in infancy and later.
(11) A method of suppressing a production of allergen-specific IgE antibodies in infancy, comprising administration of an anti-IgE antibody at a pharmaceutically effective dose to a pregnant mother and/or a child at any point from after birth to infancy, and administering an allergen to the child for additional immunotherapy.
(12) A method for suppressing IgE-class-specific immune responses during the fetal stage to infancy, comprising administration of an anti-IgE antibody at a pharmaceutically effective dose to a pregnant mother and/or a child at any point from after birth to infancy, and administration of an allergen to the child for additional immunotherapy.

(13) The combination therapy according to (11) and (12), for preventing the onset of allergic disorders in infancy and later.

(14) A method for preventing the onset of diseases in infancy and later, comprising administration of a therapeutic antibody at a pharmaceutically effective dose to a pregnant mother and/or a child at any point from after birth to infancy.

(15) An anti-IgE antibody used for suppressing production of allergen-specific IgE antibodies in infancy, which is accomplished by administration of said anti-IgE antibody to a pregnant mother and/or a child at any point from after birth to infancy.

(16) An anti-IgE antibody used for suppressing IgE-class-specific immune responses during the fetal stage to infancy, which is accomplished by administration of said anti-IgE antibodies to a pregnant mother and/or a child at any point from after birth to infancy.

(17) The anti-IgE antibody according to (15) and (16) for preventing the onset of allergic disorders in infancy and later.

(18) An anti-IgE antibody used for suppressing production of allergen-specific IgE antibodies in infancy, which is accomplished by administration of said anti-IgE antibodies to a pregnant mother and/or a child at any point from after birth to infancy, wherein the aforementioned anti-IgE antibody is used in combination with immunotherapy using an allergen that is administered to the child.

(19) An anti-IgE antibody used for suppressing IgE-class-specific immune responses during the fetal stage to infancy, which is accomplished by administration of said anti-IgE antibodies to a pregnant mother and/or a child at any point from after birth to infancy, wherein the aforementioned anti-IgE antibody is used in combination with immunotherapy using an allergen that is administered to the child.

(20) An anti-IgE antibody, which is described in (18) and (19), that prevents the onset of allergic disorders in infancy and later.

(21) A therapeutic antibody for preventing the onset of diseases in infancy and later which is accomplished by administration of said therapeutic antibody to a pregnant mother and/or a child at any point from after birth to infancy.

Effects of the Present Disclosure

By means of the present disclosure, it is possible to significantly suppress the production of allergen-specific IgE antibodies in infancy to prevent the acquisition of an allergic predisposition.

All of the contents described in the specification and drawings of Japanese Patent Application No. 2017-214455, to which the present application claims priority, are incorporated by reference in the present application.

BRIEF DESCRIPTION OF THE DRAWINGS

FIG. 1: A summary of the OVA sensitization model in neonatal mice is shown.

FIG. 2: The test results (serum OVA-specific IgE antibody titer) for the adjuvant and its administration route are shown.

FIG. 3: The test results (serum OVA-specific IgE antibody titer) for different antigen amounts are shown.

FIG. 4: The test results (decrease in body temperature after OVA administration) for different antigen amounts are shown.

FIG. 5: The test results (serum OVA-specific IgE antibody titer) for different times of analysis are shown.

FIG. 6: The scheme for evaluating anti-IgE antibody administration to pregnant mice using an OVA sensitization model is shown.

FIG. 7: The effect (serum OVA-specific IgE antibody titer) of anti-IgE antibody on neonatal mice is shown.

FIG. 8: Evaluation of the influence (serum OVA-specific IgE antibody titer) of anti-mouse IgE antibodies in serum (10-fold diluted serum) on the ELISA measurement system is shown.

FIG. 9: The effect (decrease in body temperature after OVA administration) of anti-IgE antibody administration to pregnant mice on neonatal mice is shown.

FIG. 10: The effect (serum OVA-specific IgE antibody titer) of anti-IgE antibody administration to pregnant mice on neonatal mice is shown.

FIG. 11: The effect (serum OVA-specific IgG1 antibody titer) of anti-IgE antibody administration to pregnant mice on neonatal mice is shown.

FIG. 12: The effects (serum KLH-specific IgE antibody titer; serum KLH-specific IgG1 antibody titer) of anti-IgE antibody administration to pregnant mice on neonatal mice are shown.

FIG. 13: The scheme for evaluating the duration of the suppressive effect of anti-IgE antibody administration to pregnant mice on IgE antibody production in the offspring is shown.

FIG. 14: The results (A: serum OVA-specific IgE antibody titer; B: serum OVA-specific IgG1 antibody titer) of examination of the duration of the suppressive effect of administration of anti-IgE antibodies to pregnant C57BL/6 mice on IgE antibody production in the offspring are shown.

FIG. 15: The results (A: serum OVA-specific IgE antibody titer; B: serum OVA-specific IgG1 antibody titer) of examination of the suppressive effect of anti-IgE antibody administration to pregnant BALB/c mice on IgE antibody production in the offspring are shown.

FIG. 16: The results (total IgE amount in serum) of examination of the total IgE amount in serum at the start of OVA sensitization of untreated C57BL/6 mice and untreated BALB/c mice are shown.

FIG. 17: The results (body temperature change) of examination of the effect of anti-IgE antibody administration to pregnant mice on a food allergy model in C57BL/6 and BALB/c mice are shown.

FIG. 18: The results (amounts of IL-4, IL-13, IL-17 IFN-gamma in culture supernatant) of examination of the cytokine production patterns of spleen cells from infant mice are shown.

FIG. 19: The results (serum OVA-specific IgE antibody titer) of examination of the duration of the suppressive effect of anti-IgE antibody administration to neonatal mice on IgE antibody production are shown.

FIG. 20: Explanation of the mechanism of action of administration of anti-IgE antibodies to fetuses or neonates leading to the remarkable suppressive effect on their allergen-specific IgE antibody production is shown.

MODE FOR CARRYING OUT THE PRESENT DISCLOSURE

Hereinafter, the present disclosure will be described in detail.

The present disclosure provides a pharmaceutical composition comprising an anti-IgE antibody that suppresses the production of allergen-specific IgE antibodies in infancy, which is characterized by administration of said pharmaceutical composition to a pregnant mother and/or a child at any point from after birth to infancy.

The present disclosure provides a pharmaceutical composition comprising an anti-IgE antibody for suppressing IgE-class-specific immune responses during the fetal stage to infancy, which is characterized by administration of said pharmaceutical composition to a pregnant mother and/or a child at any point from after birth to infancy.

The pharmaceutical composition of the present disclosure can prevent the onset of allergic disorders in infancy and later.

The present disclosure provides a combination therapy comprising administration of a pharmaceutical composition comprising an anti-IgE antibody and immunotherapy that administers an allergen to the child in order to suppress the production of allergen-specific IgE antibodies in infancy by administration of said pharmaceutical composition to a pregnant mother and/or a child at any point from after birth to infancy.

The present disclosure provides a combination therapy comprising administration of a pharmaceutical composition comprising an anti-IgE antibody and immunotherapy that administers an allergen to the child in order to suppress IgE-class-specific immune responses during the fetal stage to infancy by administration of said pharmaceutical composition to a pregnant mother and/or a child at any point from after birth to infancy.

The combination therapy of the present disclosure may prevent the onset of allergic disorders in infancy and later.

The present disclosure provides a pharmaceutical composition comprising a therapeutic antibody for preventing the onset of diseases in infancy and later, which is accomplished by administration of said pharmaceutical composition to a pregnant mother and/or a child at any point from after birth to infancy.

The present disclosure provides a method for suppressing production of allergen-specific IgE antibodies in infancy comprising administration of an anti-IgE antibody at a pharmaceutically effective dose to a pregnant mother and/or a child at any point from after birth to infancy.

The present disclosure provides a method of suppressing IgE-class-specific immune responses during the fetal stage to infancy, comprising administration of an anti-IgE antibody at a pharmaceutically effective dose to a pregnant mother and/or a child at any point from after birth to infancy.

The method of the present disclosure may prevent the onset of allergic disorders in infancy and later.

The present disclosure is a method of suppressing production of allergen-specific IgE antibodies in infancy, comprising administration of an anti-IgE antibody at a pharmaceutically effective dose to a pregnant mother and/or a child at any point from after birth to infancy, and administering an allergen to the child for additional immunotherapy.

The present disclosure is a method for suppressing IgE-class-specific immune responses during the fetal stage to infancy, comprising administration of an anti-IgE antibody at a pharmaceutically effective dose to a pregnant mother and/or a child at any point from after birth to infancy, and administering an allergen to the child for additional immunotherapy.

The combination therapy of the present disclosure can prevent the onset of allergic disorders in infancy and later.

The present disclosure provides a method for preventing the onset of diseases in infancy and later, comprising administration of a therapeutic antibody at a pharmaceutically effective dose to a pregnant mother and/or a child at any point from after birth to infancy.

The present disclosure provides an anti-IgE antibody for suppressing production of allergen-specific IgE antibodies in infancy, which is accomplished by administration of said anti-IgE antibody to a pregnant mother and/or a child at any point from after birth to infancy.

The present disclosure provides an anti-IgE antibody for suppressing IgE-class-specific immune responses during the fetal stage to infancy, which is accomplished by administration of said anti-IgE antibodies to a pregnant mother and/or a child at any point from after birth to infancy.

The anti-IgE antibody of the present disclosure prevents the onset of allergic disorders in infancy and later.

The present disclosure is an anti-IgE antibody for suppressing production of allergen-specific IgE antibodies in infancy, which is accomplished by administration of said anti-IgE antibodies to a pregnant mother and/or a child at any point from after birth to infancy, and it provides the aforementioned anti-IgE antibody that is used in combination with immunotherapy using an allergen that is administered to the child.

The present disclosure is an anti-IgE antibody used for suppressing IgE-class-specific immune responses during the fetal stage to infancy, which is characterized by administration of said anti-IgE antibodies to a pregnant mother and/or a child at any point from after birth to infancy, and it provides the aforementioned anti-IgE antibody that is used in combination with immunotherapy using an allergen that is administered to the child.

The anti-IgE antibody of the present disclosure that is used in combination with immunotherapy using an allergen can prevent the onset of allergic disorders in infancy and later.

The present disclosure provides a therapeutic antibody for preventing the onset of diseases in infancy and later, which is characterized by administration of said therapeutic antibody to a pregnant mother and/or a child at any point from after birth to infancy.

In the present disclosure, when the anti-IgE antibody is administered to a pregnant mother and/or a child at any point from after birth to infancy, IgE-class-specific immune responses in the child are suppressed from the fetal stage to infancy, resulting in prevention of the acquisition of an allergic predisposition.

Suppression of allergen-specific IgE antibody production can be confirmed by measuring allergen-specific IgE antibodies in the serum and by a prick test (prick test using an allergen extract or a food itself). In addition, suppression of IgE-class-specific immune responses can be confirmed by measuring allergen-specific IgE antibodies in the serum, by a prick test (prick test using an allergen extract or a food itself) and by measuring serum allergen-specific IgG antibodies.

Compared to food allergens, for which relatively large amounts of antigens are transferred to the fetus through the diet of a pregnant woman, in the case of environmental antigens such as mites and cedar pollen, there is a possibility that natural sensitization will be established more than half a year after birth. In fact, in contrast to the reports that in the case of chicken eggs and peanuts, tolerance was induced in a majority of infants by intake of these allergens (antigen transfer) in early infancy, no significant difference was found in a study in which mite antigen was administered sublingually in infancy. In the present disclosure, when natural sensitization is established more than several months after birth, it is expected that the effect of the anti-IgE antibody will be diminished. In order to establish primary prevention against environmental allergens, it can be easily inferred from the results of the present disclosure that, other than by booster inoculation of anti-IgE antibodies to an infant, prevention of IgE-class-specific immune responses may be induced by sublingual administration, etc., of mite and cedar pollen antigens, etc.—which readily act as allergens—in early infancy, when relatively high concentrations of anti-IgE antibody are present. It is often observed that sensitization is inadvertently promoted when an antigen extract used for allergen-specific immunotherapy (e.g., oral immunotherapy for chicken eggs and milk, sublingual immunotherapy for mites and cedar pollen, etc.) is administered to a naïve individual. However, based on the results of the present disclosure, even if an antigen is administered to a naïve individual, it can be expected that suppression of IgE-class-specific immune responses can be induced by administration of anti-IgE antibody and an allergen, simultaneously or separately. Here, the term 'a naïve individual' is generally assumed to be an infant within several months after birth. Another example would be when adults living in areas where there is little cedar pollen are administered anti-IgE antibodies and a cedar pollen antigen extract simultaneously, or separately within a short period of time, but these are not the only examples. In the present disclosure, when allergen immunotherapy is used in combination with a drug comprising an anti-IgE antibody, it is preferable that an antigen extract, etc., used for allergen-specific immunotherapy, etc., be administered to a naïve individual.

Table 1 shows the therapeutic antibodies currently approved in Japan, the US and Europe. In the present disclosure, the therapeutic antibodies shown in Table 1 can be used to prevent the onset of diseases in infancy and later, but they are not limited to those therapeutic antibodies.

TABLE 1

Table 1. The therapeutic antibodies currently approved in Japan, the US and Europe.

| Grouping | Name | Structure | Target molecule | Main indication disease |
|---|---|---|---|---|
| Mouse antibody | muromonab-CD3 | IgG2a | CD3 | Acute rejection after kidney transplantation |
| | ibritumomabtiuxetan | IgG1 κ (MX-DTPA: $^{90}$Y-labeled) | CD20 | B-cell non-Hodgkin lymphoma |
| | | IgG1 κ (MX-DTPA: $^{111}$in-labeled) | | Confirmation of accumulating portion of this Ab |
| | iodine131Tositumomab | IgG2a λ ($^{121}$l-labeled) | CD20 | Non-Hodgkin lymphoma |
| | catomaxomab | migG2a κ (EpCAM), rigG2b λ (CD3) | EpCAM, CD3 | Cancerous ascites |
| | blinatumomab | scFv-scFv | CD19, CD3 | Acute lymphocytic leukemia |
| Chimeric antibody | abciximab | IgG1 (Fab) | GPilb/ila | Myocardial ischemia |
| | rituximab | IgG1 κ | CD20 | B-cell non-Hodgkin lymphoma |
| | basiliximab | IgG1 κ | CD25 | Acute rejection after kidney transplantation |
| | infliximab | IgG1 κ | TNF-α | Rheumatoid arthritis |
| | cetuximab | IgG1 κ | EGFR | Head and neck cancer, colorectal cancer |
| | brentuximabvedotin | IgG1 (MMAE modification) | CD30 | Hodgkin lymphoma |
| | siltuximab | IgG1 κ | IL-6 | Castleman disease |
| | dinutuximab | IgG1 κ | GD2 | Neuroblastoma (children) |
| | obiltoxaximab | IgG1 κ | B-anthracistoxin | Inhalation anthrax |
| Humanized antibody | daclizumab | IgG1 κ | CD25 | Multiple sclerosis |
| | palivizumab | IgG1 κ | RSVFprotein | RS virus infection |
| | trastuzumab | IgG1 κ | HER2 | astatic breast cancer |
| | gemtuzumabozogamicin | IgG4 κ (Calicheamicin modification) | CD33 | Acute myeloid leukemia |
| | alemtuzumab | IgG1 κ | CD52 | B-cell chronic lymphocytic leukemia |
| | omalizumab | IgG1 κ | IgE | Asthma |
| | efalizumab | IgG1 κ | CD11 | Psoriasis vulgaris |
| | certoilzumoegol | IgG1 κ | VEGF | Colorectal cancar |
| | natalizumab | IgG1 κ | α4β7integrin | Multiple sclerosis |
| | tocilizumab | IgG1 κ | IL-6R | Castleman disease, Rheumatoid arthritis |
| | ranibizumab | IgG1 κ Fab | VEGF-A | Age-related macular degeneration |
| | eculitzumab | IgG2/4 κ | C5 | Paroxysmal nocturnal hemoglobinuria |
| | certolizumabpegol | Fab' + PEG | TNF-α | Rheumatoid arthritis, Severe Crohn's disease |
| | mogamulizumab | IgG1 κ | CCR4 | CCR4+ Adult T-cell leukemia/lymphoma |
| | pertuzmab | IgG1 κ | HER2 | HER2+ Inoperable or recurrent breast cancer |
| | trastuzumabemtansine | IgG1 κ (Maytansin modification) | HER2 | HER2+ Metastatic/recurrent breast cancer |
| | obinutumbab | IgG1 | CD20 | Chronic lymphocytic leukemia |
| | vedolizumab | IgG1 | α4β7integrin | Crohn's disease |
| | pembrolizumab | IgG4 κ | PD-1 | Melanoma |
| | idarucizumab | IgG1Fab | dabigatran | dabigatran (Pradaxa ®) neutralization |
| | mepolizumab | IgG1 κ | IL-5 | Asthma |
| | elotuzumab | IgG1 κ | 5LAMF7 | Multiple sclerosis |
| | ixekizumab | IgG4 | IL-17A | Psoriasis vulgaris |
| | reslizumab | IgG4 κ | IL-5 | Asthma |
| | atezolizumab | IgG1 κ (N298A) | PD-L1 | Urothelial cancer |
| | ocrelizumab | IgG1 | CD20 | Multiple sclerosis |
| | inotuzumabozogamicin | IgG4 κ (Ozogamicin modification) | CD22 | Acute lymphocytic leukemia |

TABLE 1-continued

Table 1. The therapeutic antibodies currently approved in Japan, the US and Europe.

| Grouping | Name | Structure | Target molecule | Main indication disease |
|---|---|---|---|---|
| | amicizumab | IgG4 κ (bispecific) | FIXa, FX | Hemophilia A |
| | benralizumab | IgG1 κ | IL-5R α subunit | Bronchial asthma |
| | galcanezumab | IgG4 | CGRP | Migraine |
| Human | adalimumab | IgG1 κ | TNF-α | Rheumatoid arthritis |
| antibody | panitumumab | IgG2 κ | EGFR | Colorectal cancer |
| | golimumab | IgG1 κ | TNF-α | Rhematioid arthritis |
| | ustekinumab | IgG1 κ | IL22, IL23-p40 | Psoriasis |
| | canakinumab | IgG1 κ | IL-1β | Cryopilin-related periodic syndrome |
| | ofatumumab | IgG1 κ | CD20 | Chronic lymphocytic leukemia |
| | denosumab | IgG2 | RANKL | Bone lesions, Osteoporosis |
| | ipillmumab | IgG1 κ | CTLA4 | Melanoma |
| | belimumab | IgG1 λ | BlyS | Systemic lupus erythematosus |
| | raxibabacumab | IgG1 λ | B.anthracistoxin | Inhalation anthrax, Lung anthrax |
| | ramucirumab | IgG1 | VEGFR2 | stomach cancer |
| | nivolumab | IgG4 | PD-1 | Malignant melanoma |
| | secukinumab | IgG1 κ | IL17-A | Psoriasis vulgaris, Arthritic psoriasis |
| | evolocumab | IgG2 | PCSK9 | hypercholesteremia |
| | alirocumab | IgG1 | PCSK9 | hypercholesteremia |
| | necitumumab | IgG1 κ | EGFR | Non-small cell lung cancer |
| | daratumumab | IgG1 κ | CD38 | Multiple myeloma |
| | brodalumab | IgG2 κ | IL17R | Psoriasis vulgaris |
| | olaratumab | IgG1 | PDGFR | Soft tissue sarcoma |
| | beztotoxumab | IgG1 | C.difficiletoxinB | Clostridium difficile infection |
| | avelumab | IgG1 λ | PD-L1 | Merkel cell carcinoma |
| | durvalumab | IgG1 κ | PD-L1 | Urothelial cancer |
| | dupilumab | IgG4 | IL-4R α | Atopic dermatitis |
| | beztotoxumab | IgG1 κ | ClostridiumdificiletoxinB | Relapse suppression of Clostridium difficile infection |
| | guselkumbab | IgG1 λ | IL-23 | Psoriasis vulgaris |
| | erilumab | IgG1 κ | IL-6R α subunit | Rhematioid arthritis |
| | burosumab | IgG1 κ | FGF23 | X chromosome hereditary hypophosphatemia |
| | erenumab | IgG2 | CGRP receptor | Migraine |

In the present specification, 'antibody' is a concept that includes those with a low molecular weight, such as Fab, F(ab)'$_2$, ScFv, diabodies, V$_H$, V$_L$, Sc (Fv)$_2$, bispecific sc (Fv)$_2$, minibodies, scFv-Fc monomer, and scFv-Fc dimer.

The anti-IgE antibody may be any of a polyclonal antibody, a monoclonal antibody, a chimeric antibody, a single-chain antibody, a humanized antibody, or a human antibody.

The anti-IgE antibody may be an antibody of IgG1, IgG2, IgG3 or IgG4, preferably an antibody of IgG1 or IgG4, and the light chain may be either κ or λ. In addition, it may be an antibody having modified sugar chains such as defucosi-fication for the purpose of enhancing its antibody dependent cellular cytotoxicity (ADCC).

Anti-IgE antibodies can be produced by the following general production methods, but the methods are not limited to these. An IgE polypeptide or a fragment including the epitope thereof is administered to an animal, and B cells that produce antibodies are recovered. Hybridoma cells are generated by fusing myeloma cells with those B cells, and a candidate antibody is selected. Alternatively, monoclonal antibodies can be obtained by a method using a chicken B cell line or a human B cell line. Or phage display methods can be used to obtain monoclonal antibodies from a library of antibody genes. Monoclonal antibodies are produced by culturing hybridoma cells. Alternatively, a monoclonal antibody is produced by culturing host cells that have been transfected with an antibody expression vector into which the selected antibody gene has been inserted. Animal cells, yeasts, insect cells, plant cells, E. coli and the like can be used as host cells. The antibodies produced by the host cells can be purified by the conventional methods used to purify proteins from culture supernatants or host cell extracts, e.g., solvent extraction, salting out, desalting, precipitation, various modes of chromatography such as ion exchange and affinity chromatography using Protein A as a ligand, membrane separation, etc., alone or in combination.

The anti-IgE antibodies can be administered to a subject by injection after it is dissolved in a buffer solution such as PBS, or physiological saline, sterile water, etc., and then sterilized by filtration with a filter, etc., as necessary. Moreover, additives (e.g., colorants, emulsifiers, suspending agents, surfactants, solubilizers, stabilizers, preservatives, antioxidants, buffers, tonicity agents, etc.) can be added to the solution.

The dose and administration route of the anti-IgE antibody may depend on the other functions (e.g., cytotoxicity, immunoglobulin effector function, etc.) associated with it, the condition of the patient (including the individual's B cell, mast cell and basophil counts), the half-life of the anti-IgE antibody, the affinity of the anti-IgE antibody for its receptors and other parameters known to the clinician.

Anti-IgE antibodies may be administered intravenously, intraperitoneally, subcutaneously, intranasally, pulmonarily, or by any other suitable route. Candidate doses can be determined using in vitro cell cultures or animal models.

Humanized anti-human IgE monoclonal antibody (Xo-lair® (trade name of omalizumab)) may be used because it is being marketed as a therapeutic agent for bronchial asthma and for chronic urticaria.

When Xolair is administered to a pregnant woman, it is basically administered with reference to the directions for use and dose described in the package insert for Xolair subcutaneous injection (67). For example, it is recommended to administer a dose of 50 to 1500 mg, preferably 75 to 600 mg, per adult, once or several times (once every 2 or 4 weeks) during the third trimester (29 to 40 weeks).

When Xolair is administered to a neonate or an infant, the dose may be decided based on the condition of the subject.

When Xolair is administered alone, continuous administration of Xolair from the neonatal stage to infancy is considered to be effective in suppressing production of allergen-specific IgE antibodies in infancy (especially early infancy). As the administration interval, it is thought that dosing once every four weeks is sufficient, as in the case of treatment of bronchial asthma. Also, when used in combination with allergen-specific immunotherapy, simultaneous administration or administration at different times within a short period, e.g., an administration method in which Xolair is administered once in the neonatal stage and once at 4-6 months after birth (i.e., the start of weaning), and then the infant is immediately exposed multiple times (e.g., daily administration for a month) to chicken eggs, peanuts, milk, mites, pollen extract, etc., is expected to be effective and practical, but the administration schedule, etc., are not limited to these methods.

In the present disclosure, the subject to which the anti-IgE antibody is administered is not limited to humans, and includes any animal capable of developing an allergic disorder.

EXAMPLES

Hereinafter, the present disclosure will be described in detail by the use of examples, but the present disclosure is not limited to these examples.

Example 1

Establishment of OVA Sensitization Model in Neonatal Mice

FIG. 1 shows the basic scheme for establishing a system for evaluating the effect of anti-mouse IgE antibody administration to pregnant mice on allergic responses in the newborn offspring. C57BL/6J mice (purchased from Japan SLC) were used, and ovalbumin (OVA) was selected as the antigen.

Basically, the evaluation system is that newborn mice were sensitized twice—on the $2^{nd}$ and $9^{th}$ days after birth—by simultaneous administration of the antigen (OVA) and an adjuvant. Blood was then drawn on the $7^{th}$ or $14^{th}$ day after the second sensitization, and the OVA-specific IgE antibody titer in the sera was evaluated. First, in order to establish this evaluation system, the type of adjuvant, the sensitization route, the amount of antigen, and the timing of blood sampling for analysis were examined.

First, for the type of adjuvant, alum (Al), an adjuvant containing mainly aluminum salt, and Complete Freund's adjuvant (CFA), an oil adjuvant, were compared. As the administration route, the intraperitoneal (i.p.) and subcutaneous (s.c.) routes were compared (FIG. 1).

Two weeks after completion of the sensitization, blood was drawn, and the separated serum was diluted 25 or 1,000 fold. The OVA-specific IgE antibody titer and the OVA-specific IgG1 antibody titer were measured by an ELISA system using biotinylated rat anti-mouse IgE antibody and biotinylated rat anti-mouse IgG1 antibody according to the standard method. Briefly, OVA was immobilized on 96-well plates (Thermo Fisher Scientific) by adding 10 μg/mL OVA to the plates and letting them stand overnight at 4° C. After washing with PBS containing 0.05% Tween 20 (Promega), the wells were blocked with PBS containing 10% FCS in order to prevent nonspecific adsorption. After washing, optimally diluted serum samples (IgE=1:25; IgG1=1:1000) were added, and the plates were incubated at room temperature for 1 hour. After washing, biotinylated rat anti-mouse IgE antibody (R35-118; BD Biosciences) and biotinylated rat anti-mouse IgG1 antibody (A85-1; BD Biosciences) were added, and the plates were incubated at room temperature for 1 hour. Then, after washing, HRP-conjugated streptavidin (Merck) was added, and the plates were incubated at room temperature for 1 hour. As an enzymatic reaction, TMB (SeraCare Life Sciences Inc.) was used as a substrate, and 1M $H_2SO_4$ was used as a stop solution. The absorbance at 450 nm was measured using a plate reader (FlexStation 3; Molecular Devices). The levels of OVA-specific IgE in the sera were measured by using an OVA-specific monoclonal antibody (TOS-2; provided by Taiho Pharmaceutical) as the standard antibody.

FIG. 2 shows the results. An increase in the OVA-specific IgE antibody titer was observed only when OVA and alum were administered intraperitoneally.

Next, when the amount of antigen to be administered is examined, the OVA-specific IgE antibody titer was seen to increase in an OVA dose-dependent manner (FIG. 3). In addition, when OVA was administered intraperitoneally 5 days after the last blood sampling and the body temperature was measured, as shown in FIG. 4, a marked decrease in body temperature was observed with both tested doses.

Finally, when the timing of blood sampling was studied, it was found that OVA-specific IgE antibody production was insufficient (below the detection sensitivity) one week after sensitization, but a detectable amount of OVA-specific IgE antibody had been produced by 2 weeks after sensitization (FIG. 5).

Study on the Inhibitory Effect of Anti-Mouse IgE Antibody on OVA-Specific IgE Antibody Production Using Pregnant Mice Based on the above results, a method (FIG. 6) for evaluating the suppressive effect of administration of anti-mouse IgE antibodies to pregnant mice on the production of OVA-specific IgE antibodies in the offspring was established, and experiments using C57BL/6J mice was conducted. Considering that maternal IgG increases in the circulation of the fetus from the second trimester in humans, 100 μg/mouse of anti-mouse IgE antibody or isotype-matched control antibody was administered to pregnant mice on embryonic day 12.5 (E12.5) and E18.5. a purified rat anti-mouse IgE antibody (R35-92: BD Biosciences) was selected as the anti-mouse IgE antibody to be administered because it is the same isotype (IgG1K) as omalizumab and its effectiveness in a murine asthma model was reported to parallel the effectiveness of omalizumab in allergic asthma patients. A purified rat IgG1K antibody (R3-34: BD Biosciences) was selected as the isotype-matched control antibody. For sensitization of the offspring to OVA, an OVA emulsion containing OVA (Sigma-Aldrich) and alum (Imuject®; Thermo Fisher Scientific) at a 1:1 ratio was administered intraperitoneally at a dose of OVA 5 μg/g mouse body weight on days 2 and 9 after birth. Sera were prepared 23 days after birth, and the body temperature reduction caused by OVA-administration was investigated 28 days after birth.

FIG. 7 shows the results. The OVA-specific IgE antibody titer increased markedly when the offspring of the mice administered the isotype-matched control antibody were sensitized with OVA, but it did not increase at all in the offspring of the mice treated with the anti-mouse IgE antibody even when they were sensitized with OVA. The anti-mouse IgE antibodies contained in the serum did not affect measurement of the antibody titer by the ELISA method (FIG. 8). Furthermore, when the effect of the intraperitoneal administration of OVA on the body temperature of the offspring mice was examined, the body temperature decreased in the offspring of mice administered the isotype-matched control antibody, but no such decrease occurred in the offspring of mice administered the anti-mouse IgE antibody (FIG. 9).

Next, the reproducibility with respect to the inhibitory effect of OVA-specific IgE antibody production in the offspring of pregnant mice treated with anti-mouse IgE antibody was tested (FIG. 7). As shown in FIG. 10, the increase in the OVA-specific IgE antibody titer caused by OVA sensitization was completely suppressed in the offspring of the mice treated with the anti-mouse IgE antibody, which shows that this effect is highly reproducible.

It is known that simultaneous intraperitoneal administration of alum and OVA elicits production of not only OVA-specific IgE antibodies but also OVA-specific IgG1 antibodies. Therefore, the OVA-specific IgG1 antibody titer in serum by the ELISA system using the biotinylated rat anti-mouse IgG1 antibody (A85-1: BD Bioscience) was examined. As shown in FIG. 11, when the offspring of mice administered anti-mouse IgE antibody and the offspring of mice injected with isotype-matched control antibody were sensitized with OVA, it was found that both offspring produced OVA-specific IgG1 antibodies at the same level.

Next, in order to investigate whether or not similar results were obtained for other allergens, KLH (keyhole limpet hemocyanin) was used instead of the OVA emulsion. Specifically, offspring were sensitized by intraperitoneal administration of an emulsion of KLH and alum (KLH:alum=1:1) at a dose of KLH 0.25 μg/bodyweight (g) on days 2 and 9 after birth, and a similar experiment was performed (FIG. 12). As a result, when the offspring of the mice treated with the isotype-matched control antibody were sensitized with KLH, a marked increase in the KLH-specific IgE antibody titer was observed, but there was no increase in the offspring of the mice treated with the anti-mouse IgE antibody (FIG. 12). In contrast, both offspring produced KLH-specific IgG1 antibodies at the same level. This finding that the results are the same regardless of whether the allergen is OVA or KLH suggests the possibility that when anti-mouse IgE antibodies are administered to pregnant mice, the production of IgE antibodies specific to various allergens is remarkably suppressed in their offspring.

Because both allergen-specific IgE antibodies and allergen-specific IgG1 antibodies are produced by B cells, the above findings suggest that the complete suppression of allergen-specific IgE antibody production in the offspring of mice treated with anti-IgE antibodies was caused not by the destruction of B cells but by specific suppression of the production pathway of IgE antibodies.

Study on the Duration of the Suppression of OVA-Specific IgE Antibody Production in Offspring Next, the following experiment was conducted in order to clarify the duration of complete suppression of the capacity of offspring to produce OVA-specific IgE antibodies. Anti-mouse IgE antibody or isotype-matched control antibody was administered at 100 μg/mouse to pregnant mice at E12.5 and E18.5. The offspring were divided into 4 groups, and sensitization was started from four different time points (2, 16, 30 or 44 days after birth) (FIG. 13). Sensitization by intraperitoneal administration of 5 μg/body weight (g) of OVA and alum to offspring was started at 0 weeks after birth (2 and 9 days after birth) in Protocol A, 2 weeks after birth (16 and 23 days after birth) in Protocol B, 4 weeks after birth (30 and 37 days after birth) in Protocol C, or 6 weeks after birth (44 and 51 days after birth) in Protocol D (FIG. 13). Two weeks after the final sensitization, blood was collected, and the OVA-specific IgE antibody titer and OVA-specific IgG1 antibody titer were measured (FIGS. 14A and 14B). As shown in FIG. 14A, when the offspring of mice treated with the isotype-matched control antibody were sensitized at any time from 0, 2, 4 or 6 weeks after birth, a marked increase in the OVA-specific IgE antibody titer was observed, but when the offspring of mice treated with anti-mouse IgE antibody were sensitized with OVA, the production of OVA-specific IgE antibodies was completely inhibited. On the other hand, as shown in FIG. 14B, when offspring of mice treated with the anti-mouse IgE antibody and offspring of mice treated with the isotype-matched control antibody were sensitized with OVA according to any of the protocols, they all produced OVA-specific IgG1 antibodies at the same level.

The half-lives of mouse and human IgG antibodies are 6-8 days and 22-23 days, respectively. Considering that 6 weeks of age in mice corresponds to 3-4 months of age in humans by conversion from the half-life of IgG, the above results are thought to indicate a strong possibility of complete suppression of IgE antibody production for up to 3-4 months after birth in infants by administering anti-IgE antibodies to pregnant women in the third trimester.

Because all the results described above were generated in C57BL/6 mice, the same experiment as that shown in FIG. 13 was carried out using a different strain, BALB/c mice, and the OVA-specific IgE antibody and OVA-specific IgG1 antibody titers were similarly measured. As a result, even in the case of BALB/c mice, the administration of anti-mouse IgE antibodies to pregnant mice did not affect their offspring's production of OVA-specific IgG1 antibodies, but it completely inhibited production of OVA-specific IgE antibodies by the offspring in the case of Protocol A (FIG. 15A). However, because no inhibitory effect on the production of OVA-specific IgE antibodies was observed in the other protocols, a strain difference was observed with respect to the duration of the suppression of IgE antibody production. On the other hand, with each of the protocols, when offspring of mice treated with anti-mouse IgE antibody and offspring of mice injected with isotype-matched control antibody were sensitized with OVA, all the offspring produced OVA-specific IgG1 antibodies at the same level (FIG. 15B).

In order to investigate the cause of the above strain difference, naïve C57BL/6 and BALB/c mice was used, and the amount of total IgE antibody in the serum was measured at the starting point of sensitization with each of the four protocols by the following method.

Briefly, rat IgG anti-mouse IgE (R35-72, BD Biosciences) was immobilized on 96-well plates by adding 2 μg/mL of the antibody to each well, and the plates were allowed to stand overnight at 4° C. After washing with PBS containing 0.05% Tween 20, blocking was performed with PBS containing 10% FCS in order to avoid non-specific adsorption. Optimally-diluted serum samples (25 fold) were applied, and the plates were incubated at room temperature for 1 hour. After washing, biotinylated rat anti-mouse IgE (R35-118; BD Biosciences) was added to the wells, and the plates were incubated at room temperature for 1 hour. Then, after washing, HRP-conjugated streptavidin was added, followed by incubation at room temperature for 1 hour. As an enzymatic reaction, TMB was used as a substrate, and 1M $H_2SO_4$ was used as a stop solution. The absorbance at 450 nm was measured using a plate reader. The levels of total IgE in the sera were measured by using a mouse IgE monoclonal Ab (C38-2, BD Bioscience) as the standard antibody.

As a result, in the case of the low-IgE-responder C57BL/6 mice, the total IgE antibody level in the serum was below the limit of detection until postnatal day 30 (PND30). On the other hand, in the case of the high-IgE-responder BALB/c mice, 500 ng/mL or more of total IgE antibody was detected on and after PND30 (FIG. 16).

Because the amount of serum IgE antibody remains at a very low level pre- and postpartum, membrane-bound IgE receptor positive (mIgE+) B cells, which can hardly be detected in vivo, are considered to be the only target for anti-IgE antibodies transferred to the fetal immune system. In this light, it is possible to explain that the anti-mouse IgE antibody was able to markedly suppress IgE production in C57BL/6 mice in infancy, when the baseline of total IgE antibody remained at a low level. In addition, because BALB/c mice had a clearly higher amount of total IgE antibody at the starting points of antigen sensitization than the C57BL/6 mice, the probability of anti-IgE antibodies binding to mIgE on B cells might be decreased, which is thought to be one of the causes of the above-mentioned difference in the duration of suppression of allergen-specific IgE antibody production in the two strains. Here, in the case of a high IgE responder (similar to BALB/c mice), one may have doubts that anti-IgE antibody can effectively suppress IgE production. However, in the case of humans, the results may be similar to those of C57BL/6 mice based on the finding that the level of total IgE antibody remains low in human infancy. In any event, whereas serum IgE levels in humans remain very low for several months after birth, in BALB/c mice serum IgE levels increase dramatically as they grow to adults by several weeks after birth. For that reason, the interpretation of the results of the present disclosure, a preclinical study, based on the findings generated in BALB/c mice may lead to a serious misunderstanding when predicting the clinical results. The results generated in C57BL/6 mice is discussed.

Furthermore, in order to investigate the effects of anti-mouse IgE antibody administration to pregnant mice on food allergies in their offspring, 10 μg/body weight (g) of OVA was administered intraperitoneally to offspring 5 days after blood collection, and their rectal temperature was measured at 0, 10, 20, 30, 40, 50 and 60 minutes after the OVA administration. In the case of C57BL/6 mice, administration of anti-mouse IgE antibody to pregnant mice was able to significantly suppress the decrease in body temperature in Protocol A, and reproducibility of the results shown in FIG. 9 was demonstrated. However, no suppressive effect of administration of anti-IgE antibody on body temperature decrease was observed in Protocols B, C and D. On the other hand, in the case of BALB/c mice, the administration of anti-mouse IgE antibody to pregnant mice showed a tendency to suppress the body temperature decrease in Protocol A, but not in Protocol B (FIG. 17). As mentioned above, in the case of Protocol A, the response to the challenged allergen was attenuated in both strains, but no clear attenuation was observed in the other protocols. The cause of this is thought to be that an IgG-mediated, but not IgE-mediated, allergic response was induced by the OVA administration. Because the responses in food allergy models differ greatly between humans and rodents and IgE-mediated allergic responses occur mainly in humans, it is highly likely that these results generated in mice are not fully applicable to humans.

Study on Status of T Cell Differentiation in Offspring Mice

In addition, 3 days after measuring the rectal temperature, spleen cells were prepared from the offspring of C57BL/6 mice whose rectal temperature was measured as shown in FIG. 17. The spleen cells were cultured for 96 hours in the presence or absence of OVA (200 μg/mL), and IL-4, IL-13, IL-17 and interferon-γ (IFN-γ) in the culture supernatants were quantified by ELISA. Briefly, spleen cells were harvested from each mouse 3 days after measuring the rectal temperature. Spleen cell suspensions were prepared using a 70-μm cell strainer (Corning), followed by erythrocyte lysis with a lysing buffer (BioLegend). The spleen cell suspensions were cultured at 37° C. in 48-well plates at $2×10^6$ cells/mL in RPM11640 (Nacalai Tesque) containing 10% FCS (Biological Industries), 100 U/mL penicillin and 100 mg/mL streptomycin (Thermo Fisher Scientific) in the presence and absence of 200 μg/mL OVA. Culture supernatants were harvested after 96-hour incubation, and the levels of the above cytokines in the culture supernatants were determined using ELISA kits (Thermo Fisher Scientific) according to the manufacturer's instructions.

FIG. 18 shows the results. When spleen cells prepared from offspring sensitized with OVA were cultured with OVA (OVA stimulation), the productions of IL-4 and IL-13 were markedly and significantly higher compared with the case without OVA (no stimulation). However, when the offspring of mice treated with isotype-matched control antibody or anti-mouse IgE antibody was compared, the amounts of IL-4 and IL-13 produced upon OVA stimulation did not differ significantly between the two treatment groups. Regarding IFN-γ, spleen cells stimulated with OVA showed markedly and significantly increased IFN-γ production compared with without stimulation. However, when offspring of mice treated with isotype-matched control antibody or anti-mouse IgE antibody were compared, they showed no significant difference in the amount of IFN-γ produced upon OVA stimulation. Regarding IL-17, although spleen cells cultured with OVA showed a tendency for increased IL-17 production compared to the case without OVA, no significant difference was found between the offspring of mice treated with isotype-matched control antibody or anti-mouse IgE antibody.

The process by which naïve T cells acquire the function of helper cells is called differentiation, and the direction of differentiation is defined by antigen stimulation of naïve T cells in a particular cytokine milieu. Differentiated helper T cells are classified into Th1 (IFN-γ), Th2 (IL-4, IL-13), Th17 (IL-17), Treg, etc., based on their cytokine production pattern. As shown in FIG. 18, when spleen cells prepared from offspring of mice treated with the anti-mouse IgE antibody or the isotype-matched control antibody were stimulated with OVA, they showed no significant differences in their production patterns of IL-4, IL-13, IL-17 and IFN-γ. These findings suggest that suppression of OVA-specific IgE antibody production in the offspring of mice treated with anti-mouse IgE antibody was caused not by suppression of differentiation into Th2 cells (which play an important role in IgE antibody production), or by stimulation of differentiation into Th1 cells (which inhibit differentiation into Th2 cells), but by direct suppression of IgE production by B cells.

Study on the Duration of the Suppression of OVA-Specific IgE Antibody Production Induced by Anti-IgE Antibody Administration to Newborn Mice Next, the inhibitory effect on the production of OVA-specific IgE antibodies and its duration were investigated when anti-IgE antibody was administered to neonatal mice. Anti-mouse IgE antibody (10 μg/mouse) or isotype-matched control antibody was administered to C57BL/6 neonatal mice one day after birth. Sensitization by intraperitoneal administration of OVA 5 μg/body weight (g) and alum to the neonatal mice was started at 0 weeks of age (2 and 9 days after birth) in G1 Group, at 2 weeks after birth (16 and 23 days after birth) in G2 group, or at 6 weeks after birth (44 and 51 days after birth) in G4 group. Two weeks after the final sensitization, blood was collected and the OVA-specific IgE antibody titer was measured (FIG. 19A). As a result, as shown in FIG. 19B, regardless of whether OVA sensitization was started from 0, 2 or 6 weeks after birth, mice that had been treated with isotype-matched control antibody in the neonatal period showed a marked increase in the OVA-specific IgE antibody titer. In contrast, mice treated with anti-mouse IgE antibody in the neonatal period and then similarly sensitized with OVA showed absolutely no increase in the OVA-specific IgE antibody titer. These findings regarding the inhibitory effect of administration of anti-mouse IgE antibody to newborn mice on their OVA-specific IgE antibody production and its duration are the same as those obtained when anti-mouse IgE antibody was administered to pregnant mice (FIG. 14A).

Discussion

The above results revealed that administration of an anti-mouse IgE antibody (like omalizumab, an IgG1 kappa antibody) to pregnant C57BL/6 mice completely suppresses production of allergen-specific IgE antibodies, which play important roles in the development and progression of allergic disorders, in the offspring. Yet, it does not affect production of T cell-derived cytokines (IL-4, IL-13, IL-17 and IFN-γ) in response to allergen stimulation or production of allergen-specific IgG1 antibodies, which play important roles in protection against infectious diseases. It was also found that almost complete inhibition of allergen-specific IgE antibody production persists for at least 6 weeks in mice (corresponding to 3-4 months in humans). On the other hand, when the anti-mouse IgE antibody was administered to pregnant BALB/c mice, the inhibition of allergen-specific IgE antibody production was much shorter in duration than in C57BL/6 mice. As one of the causes, it is thought that because the total IgE antibody levels following allergen sensitization in BALB/c mice were clearly higher than those in C57BL/6 mice, there might be a lower probability of anti-IgE antibodies binding to mIgE on B cells. Considering that the level of total IgE antibody remains low in humans during infancy, it is presumed that the results in humans will be similar to those obtained in C57BL/6 mice.

Furthermore, in an evaluation system using C57BL/6 neonatal mice, it was found that administration of the anti-mouse IgE antibody to the neonatal mice specifically suppressed the production of allergen-specific IgE antibodies for at least 6 weeks.

The neonatal Fc receptor for IgG (FcRn) is known to play an important role in IgG transfer from mother to fetus. In the case of rats and mice, it is known that before birth maternal serum IgG is transferred to the fetus via FcRn expressed in the yolk sac, while after birth IgG in breast milk is transferred into the blood of neonatal mice via their intestinal FcRn. Administration of IgE antibodies to mice in the neonatal period was reported to cause relatively long-term suppression of IgE antibody production; as the possible mechanism of action, it was proposed that anti-IgE antibodies were produced in the mice. Taking that report and the above findings into consideration, it is surmised that the results obtained in this disclosure are due to a process in which the anti-mouse IgE antibodies (IgG1κ) administered to the mother mice were transferred to the fetuses and newborns, where the transferred antibodies exerted their efficacy, leading to suppression of allergen-specific IgE antibody production.

In the case of humans, it is known that maternal IgG is transferred to the fetus through the placenta. Therefore, it is thought that if a therapeutic antibody is administered to a pregnant woman after the third trimester, when FcRn is expressed in the placenta, there is a strong possibility that the antibody will be transferred to the fetus. Taking these findings together, it is thought that when omalizumab is administered to a pregnant woman in the third trimester, it will be transferred to the fetus because it is an IgG1κ isotype antibody. This concept is supported by a report that omalizumab passed through the placenta in animal experiments using cynomolgus monkeys.

Taken together, the results in the C57BL/6 mice shown in the Examples can be thought to indicate that when a highly safe therapeutic anti-IgE antibody, omalizumab, is administered to pregnant women, the antibody is transferred to the fetus. It then selectively prevents production of allergen-specific IgE antibodies, which play important roles in allergic responses (can suppress IgE-class-specific immune responses) in infants for at least 3-4 months after birth without affecting the production of allergen-specific IgG1 antibodies, which are important for defense against infections. As a result, there is a strong possibility of preventing development of subsequent allergic disorders, especially development of food allergies and production of IgE antibodies specific to universal allergens (acquisition of a so-called allergic predisposition).

It was found that administration of anti-mouse IgE antibody to pregnant mice is able to almost completely inhibit allergen-specific IgE antibody production in the offspring, and its mechanism of action is surmised to be as follows.

Although, generally, there are three kinds of targets of anti-IgE antibody, i.e., (1) free IgE, (2) membrane-anchored IgE (mIgE) on B cells and (3) IgE bound to CD23, it is thought that mIgE positive (mIgE+) B cells are almost the sole target of anti-IgE antibody during the fetal to infancy period because there is little or no free IgE. Because mIgE+ B cells are barely detectable in vivo, much remains unclear regarding their functions and dynamics. However, based on the results of in vitro tests such as forced expression systems, because mIgE+ B cells have various mechanisms that more readily cause apoptosis compared to other membrane-bound immunoglobulin-positive B cells such as mIgG+, apoptosis of mIgE+ B cells is easily induced by binding of anti-IgE antibody, etc., to mIgE near the membrane, except in the presence of co-stimulation with IL-4 and CD40L. Although anergy, rather than apoptosis, is thought to be the mechanism of action of omalizumab, in any case it acts as an inhibitor of production of IgE antibodies. Considering these findings, the results in the C57BL/6 mice shown in the Examples (FIG. 14A) can be interpreted as meaning that the therapeutic anti-IgE antibodies were transferred to the fetus, bound to mIgE+ cells that appeared upon sensitization/induction of immunity (after birth) near the membrane and induced apoptosis or anergy of B cells, leading to complete suppression of production of IgE (FIG. 20, fetal period to infancy). When spleen cells of the offspring of mice administered anti-mouse IgE antibody or isotype-matched control antibody were stimulated with OVA, their production patterns of IL-4, IL-13, IL-17 and FN-γ were similar (FIG. 18). That finding is considered to support the above interpretation that the complete suppression of IgE production was induced not by suppression of differentiation to Th2 cells, which play an important role in the production of IgE antibodies, or by promotion of differentiation into Th1 cells, which inhibit differentiation to Th2 cells, but by direct suppression of the IgE antibody production system in B cells. When the anti-mouse IgE antibody was administered to newborn mice, the inhibitory effect on OVA-specific IgE antibody production and the duration of the suppressed state were almost the same as when the antibody was administered to pregnant mice. These results (FIG. 14A and FIG. 19) are thought to indicate that neonatal mIgE+ B cells have similar properties to those of fetal mIgE+ B cells.

On the other hand, in early childhood to adulthood, although it was reported that omalizumab does not bind to IgE that is bound to CD23, the targets of anti-IgE antibody are generally considered to be (1) free IgE, (2) mIgE on B cells and (3) IgE bound to CD23. Therefore, since unlike in the fetal stage, in infants and adults free IgE is overwhelmingly abundant, meaning that when anti-IgE antibody is administered the antibody will hardly reach mIgE+ B cells. Omalizumab is used clinically to prevent exacerbation of allergic disorders by inhibiting the binding of free IgE to mast cells of allergic patients (FIG. 20, infancy-adult).

The inventors of Genentech Inc. specified in the above-mentioned patents (U.S. Pat. No. 6,685,939, JP3457962) that "The FcεH and FcεL-specific polypeptides and anti-IgE antibodies (especially those with reduced immunogenicity) are useful in therapies for the treatment or prophylaxis of allergies, otherwise, the polypeptides typically are administered to a patient who is known to be sensitized to an allergen, preferably prior to an acute allergic response." That is, the inventors of Genentech Inc. envisioned that the polypeptides and anti-IgE antibodies would be useful for patients who have already been sensitized to an allergen and as therapeutic agents in order to alleviate symptoms when acute allergic responses occur, and that, preferably, the polypeptides and anti-IgE antibodies should be used prophylactically prior to an acute allergic response in order to prevent its manifestation (because this means prevention of exacerbation of asthma symptoms, etc., the aim is tertiary prevention). In fact, omalizumab is being used clinically to prevent exacerbation of allergic disorders by inhibiting the binding of free IgE to mast cells of allergic patients. In addition, a clinical trial is being planned in the USA to study the preventive effects of omalizumab on the onset of asthma in 2- to 3-year old children who have already been sensitized to aeroallergens such as mites, but have not yet developed asthma (secondary prevention).

In contrast, the aim of the present disclosure is prevention of sensitization (primary prevention) of fetuses, newborns and infants who are not yet sensitized to universal allergens. The present disclosure is based on the strategy of preventing acquisition of an allergic predisposition via complete suppression of IgE production for up to 3-4 months after birth. Accordingly, it is clear that Genentech's invention and the present disclosure have completely different target subjects and aims.

In the case of food allergens, relatively large amounts of antigens are transferred to the fetus through the diet of the pregnant mother, whereas in the case of environmental antigens such as mites and cedar pollen, it may be possible for natural sensitization to be established subsequent to 6 months of age. In fact, as noted above in "Induction of tolerance (immune tolerance) by antigen transfer", although it was reported that tolerance to chicken eggs and peanuts was induced in a majority of infants by intake of these allergens (antigen transfer) in early infancy, no significant difference was found in a study in which mite antigens were administered sublingually during infancy. In the present disclosure, when natural sensitization is established several months after birth, it is expected that the effect of anti-IgE antibodies administered to a pregnant woman or a neonate will be diminished. Besides supplementation with anti-IgE antibodies in infants, sublingual administration of antigens such as mites and cedar pollen in early infancy, when relatively high concentrations of anti-IgE antibody are present, can be thought to be effective for preventing sensitization to environmental antigens, i.e., establishment of primary prevention. This concept can be easily inferred from the results of the present disclosure that IgE-class-specific immunosuppression was induced by these treatments. It has been observed that sensitization is often promoted when naïve (unsensitized) individuals are administered an antigen extract used for immunotherapy specific for an allergen, such as by sublingual immunotherapy. However, based on the results of the present disclosure, even in the case of administration of an antigen to naïve individuals, suppression of IgE-class-specific immune responses can be expected to be induced by administration of anti-IgE antibodies and the antigen, simultaneously or separately. Here, the term 'naïve (unsensitized) individuals' generally means infants within several months after birth. Administration of anti-IgE antibodies and a cedar pollen antigen extract simultaneously, or separately within a short period of time, to adults living in areas where there is little cedar pollen can be considered another example, but these are not the only examples.

As described above, the present inventors have discovered a method for preventing neonatal IgE production, completely or almost completely, up to at least 3-4 months of age. Regarding the effects of prevention of IgE production for prolonged periods, the published information on IgE-deficient mice can be considered to be informative. No apparent abnormalities, including of the phenotype, under normal breeding conditions were reported in IgE-deficient SJA/9 mice or IgE knockout BALB/c mice. IgE antibodies play important roles in protection against parasitic infections. When both of those mouse strains were infected with Trichinella spiralis, it was found that even when parasitic infections occurred under IgE-deficient conditions, protection against the infection in IgE-deficient SJA/9 mice was established similarly to in the wild type mice, while it was established a bit later in the IgE knockout BALB/c mouse compared with the wild type mice. In consideration of the results described above, it can be surmised that IgE-specific deficiency does not exert harmful effects in normal life.

Furthermore, a 52-week, randomized, double-blind placebo-controlled clinical study of 137 patients with asthma or rhinitis who were at high risk of intestinal parasite infection found that the omalizumab group showed no significant increase in the risk of parasite infection compared to the control group, and that there was no difference in the response to anti-parasitic therapy between the groups. Those findings support the above assertion that complete inhibition of IgE production in infants for several months will not have harmful effects.

The following are known examples of treating a fetal disease by administering drugs to the mother. 1) A placenta-permeable steroid is administered to the mother for fetal congenital atrioventricular block caused by maternal anti-SS-A antibodies. 2) For fetal heart failure due to maternal hyperthyroidism (Basedow's disease), high doses of anti-thyroid drugs are administered to the mother. 3) Antiarrhythmic drugs are given to the mother for fetal tachyarrhythmia.

On the other hand, the present inventors proposed a method for suppressing IgE production in fetuses by administration of a therapeutic antibody drug to the mothers. Others suggested the possibility that the method of transfer of IgG antibodies from mother to fetus via FcRn expressed on the placenta, etc., might be useful for therapy of fetal diseases. Also, it was reported that in a beta-glucuronidase (GUS)-deficient mouse model, injection of the GUS-Fc fusion protein, although it is not an IgG antibody, into pregnant mice inhibited excessive lysosome accumulation in the offspring. And as a clinical case, it was reported that when a mother was pregnant with a child with XLHED (X-linked hypohidrotic ectodermal dysplasia), treatment was attempted by administration of Fc-EDA (the Fc of immunoglobulin is bound to ectodysplasin A (EDA)) to the pregnant mother. However, as far as the inventors are aware, no attempt has been made to prevent or treat diseases in offspring by transferring therapeutic antibodies to the fetus through the mother. Thus, the present disclosure is thought to show highly novel examples in terms of practical new methods of administration of therapeutic antibodies.

The inventors conceived a preventive method for allergic disorders in infancy in which a therapeutic IgG antibody such as omalizumab that possesses anti-human IgE antibody activity is administered to pregnant women, and the therapeutic antibody is transferred to the fetus via FcRn, which is strongly expressed in placental tissue. The transferred antibodies bind to membrane-anchored IgE on fetal B cells, resulting in prevention of production of IgE antibodies in the offspring from the fetal stage to early infancy (i.e., prevention of IgE-class-specific immune responses in the offspring from the fetal stage to early infancy). And the relevance of our preventive method for allergic disorders in infancy has been proven by our findings in an evaluation system using pregnant mice. That is, when an anti-mouse IgE antibody (an IgG1 kappa antibody, which is the same as omalizumab) was administered to pregnant mice, it was possible to selectively inhibit production of allergen-specific IgE antibodies in the offspring for at least 6 weeks (equivalent to 3-4 months in humans). Taking into account the transfer mechanism of therapeutic IgG antibodies to the fetus via FcRn, it is thought that our present results generated in mouse experiments can be extrapolated to humans.

Furthermore, in an evaluation system using neonatal mice, that when an anti-mouse IgE antibody (an IgG1 kappa antibody, which is the same as omalizumab) was administered to neonatal mice, it was possible to selectively inhibit production of allergen-specific IgE antibodies for at least 6 weeks.

Omalizumab, a therapeutic anti-IgE antibody, is widely used in humans for intractable allergic disorders such as asthma and chronic urticaria. It is known that it alleviates the symptoms of those allergic disorders through the mechanism of neutralizing free IgE antibodies in the serum, that it has few adverse effects, and that it has been safely administered to pregnant women.

Based on above, it can be thought that if a highly safe anti-IgE antibody such as omalizumab is administered to a pregnant woman and/or a child at any point from the newborn stage to infancy, it is fully possible to prevent production of allergen-specific IgE antibodies, i.e., to prevent acquisition of an allergic predisposition, in infancy.

The scope of the claims:

1. A method of decreasing a risk of an allergic predisposition in a subject, the method comprising
   administering an effective amount of an anti-IgE antibody to the subject, and
   administering an effective amount of an allergen to the subject,
   wherein the subject is not sensitized to an allergen that causes the allergic predisposition and is in infancy or younger; and
   the anti-IgE antibody is administered during a newborn stage, an early infancy, or an infancy, or the anti-IgE antibody is full-length.

2. A method of suppressing production of allergen-specific IgE antibodies in a subject, comprising administering an effective amount of an anti-IgE antibody to the subject, wherein the subject is not sensitized to an allergen that causes the allergic predisposition and is in infancy or younger.

3. The method according to claim 1, wherein the subject is human.

4. The method according to claim 1, wherein the method comprises administering the effective amount of the anti-IgE antibody to a mother pregnant with the subject.

5. The method according to claim 4, wherein the mother is not diagnosed with asthma.

6. The method according to claim 4, wherein the mother is not diagnosed with an allergic disorder.

7. The method according to claim 1, wherein the subject is not diagnosed with asthma.

8. The method according to claim 1, wherein the subject is not diagnosed with an allergic disorder.

9. The method according to claim 1, wherein the method comprises administering the effective amount of the anti-IgE antibody to the subject during the newborn stage.

10. The method according to claim 1, wherein the method comprises administering the effective amount of the anti-IgE antibody to the subject during the early infancy.

11. The method according to claim 1, wherein the method comprises administering the effective amount of the anti-IgE antibody to the subject during the infancy.

12. The method according to claim 1, wherein the method decreases a probability for an onset of an allergic disorder in the subject during infancy and later.

13. The method according to claim 1, wherein the allergen is food allergen.

14. The method according to claim 1, wherein the allergen comprises peanut.

15. The method according to claim 1, wherein the anti-IgE antibody comprises omalizumab.

16. The method according to claim 4, wherein the mother has not taken the anti-IgE antibody previously.

17. The method according to claim 1, wherein the anti-IgE antibody is a full-length IgG.

* * * * *